United States Patent
Roth et al.

(10) Patent No.: US 6,561,998 B1
(45) Date of Patent: *May 13, 2003

(54) TRANSLUMINAL DEVICES, SYSTEMS AND METHODS FOR ENLARGING INTERSTITIAL PENETRATION TRACTS

(75) Inventors: Alex T. Roth, Redwood City, CA (US); J. Christopher Flaherty, Los Altos, CA (US); Adrian E. Johnson, Stockton, CA (US); Joshua Makower, Los Altos, CA (US); Jason Brian Whitt, San Francisco, CA (US)

(73) Assignee: TransVascular, Inc., Menlo Park, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/056,589

(22) Filed: Apr. 7, 1998

(51) Int. Cl.⁷ .................................. A61B 17/20
(52) U.S. Cl. ............................................. 604/22
(58) Field of Search .................. 606/192, 33, 41, 606/45–48, 50; 604/22, 107, 108, 500, 507, 508, 506, 510

(56) References Cited

U.S. PATENT DOCUMENTS

| | | | |
|---|---|---|---|
| 3,920,021 A | 11/1975 | Hiltebrandt | 128/303.17 |
| 3,974,833 A | 8/1976 | Durden, III | 128/275.1 |
| 4,589,412 A | 5/1986 | Kensey | 128/305 |
| 4,681,106 A | 7/1987 | Kensey et al. | 128/305 |
| 4,682,596 A * | 7/1987 | Bales et al. | |
| 4,693,556 A | 9/1987 | McCaughan, Jr. | 350/320 |
| 4,805,616 A | 2/1989 | Pao | 128/303.17 |
| 4,867,138 A * | 9/1989 | Kubota et al. | 128/6 |
| 4,886,061 A | 12/1989 | Fischell et al. | 128/305 |

(List continued on next page.)

FOREIGN PATENT DOCUMENTS

| | | | |
|---|---|---|---|
| WO | 9517131 | 6/1995 | A61B/17/39 |
| WO | 9717100 | 5/1997 | A61M/29/00 |
| WO | 9732532 | 9/1997 | A61B/17/39 |
| WO | 9733522 | 9/1997 | A61B/17/32 |
| WO | 9825533 | 6/1998 | A61B/17/39 |
| WO | 9838939 | 9/1998 | |
| WO | 9838941 | 9/1998 | A61B/19/00 |
| WO | 9838942 | 9/1998 | A61B/19/00 |
| WO | 9901074 | 1/1999 | A61B/17/36 |

Primary Examiner—Anhtuan T. Nguyen
Assistant Examiner—Ann Lam
(74) Attorney, Agent, or Firm—Robert D. Buyan; Stout, Uxa, Buyan & Mullins, LLP

(57) ABSTRACT

Methods, apparatus and systems for enlarging interstitial penetration tracts which have been formed between blood vessels or elsewhere within the body of a mammalian patient. Included are debulking-type tract enlarging systems, dilation-type tract enlarging systems, tissue-slicing-type tract enlarging systems and two-catheter-type tract enlarging systems.

5 Claims, 19 Drawing Sheets

U.S. PATENT DOCUMENTS

| | | | |
|---|---|---|---|
| 4,998,933 A | 3/1991 | Eggers et al. | 606/41 |
| 5,011,490 A | 4/1991 | Fischell et al. | 606/159 |
| 5,078,717 A * | 1/1992 | Parins et al. | 606/48 |
| 5,100,425 A | 3/1992 | Fischell et al. | 606/159 |
| 5,127,902 A | 7/1992 | Fischell | 604/22 |
| 5,129,913 A | 7/1992 | Ruppert | 606/184 |
| 5,372,603 A | 12/1994 | Acker et al. | 606/194 |
| 5,403,338 A | 4/1995 | Milo | 606/184 |
| 5,409,454 A | 4/1995 | Fischell et al. | 604/22 |
| 5,423,846 A | 6/1995 | Fischell | 606/180 |
| 5,522,834 A | 6/1996 | Fonger et al. | 606/194 |
| 5,527,325 A | 6/1996 | Conley et al. | 606/159 |
| 5,556,397 A | 9/1996 | Long et al. | 606/48 |
| 5,599,345 A | 2/1997 | Edwards et al. | 606/41 |
| 5,613,972 A | 3/1997 | Lee et al. | 606/107 |
| 5,620,439 A | 4/1997 | Abela et al. | 606/11 |
| 5,628,761 A | 5/1997 | Rizik | 606/170 |
| 5,628,762 A | 5/1997 | Al-Tameem | 606/170 |
| 5,643,257 A | 7/1997 | Cohen et al. | 606/48 |
| 5,643,296 A | 7/1997 | Hundertmark et al. | 606/159 |
| 5,662,671 A | 9/1997 | Barbut et al. | 606/170 |
| 5,665,062 A | 9/1997 | Houser | 604/22 |
| 5,672,171 A | 9/1997 | Andrus et al. | 606/15 |
| 5,685,320 A | 11/1997 | Zimmon et al. | 128/754 |
| 5,725,521 A | 3/1998 | Mueller | 606/7 |
| 5,725,543 A | 3/1998 | Redha | 606/159 |
| 5,741,270 A | 4/1998 | Hansen et al. | 606/108 |
| 5,755,697 A | 5/1998 | Jones et al. | 604/174 |
| 5,776,114 A | 7/1998 | Frantzen et al. | 604/281 |
| 5,800,378 A * | 9/1998 | Edwards et al. | 604/22 |
| 5,827,315 A | 10/1998 | Yoon | 606/185 |
| 5,827,324 A | 10/1998 | Cassell et al. | 606/200 |
| 5,843,019 A | 12/1998 | Eggers et al. | 604/22 |
| 5,843,103 A | 12/1998 | Wulfman | 606/159 |
| 5,957,900 A * | 9/1999 | Ouchi | 604/264 |
| 6,047,700 A * | 4/2000 | Eggers et al. | 128/898 |

* cited by examiner

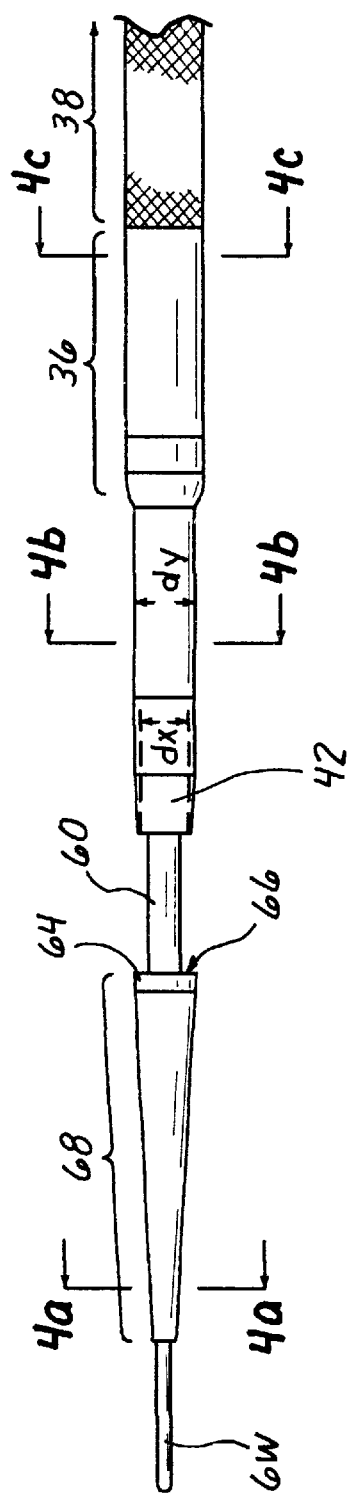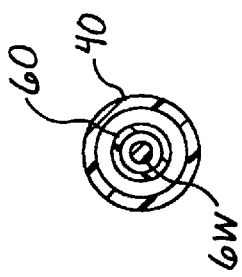

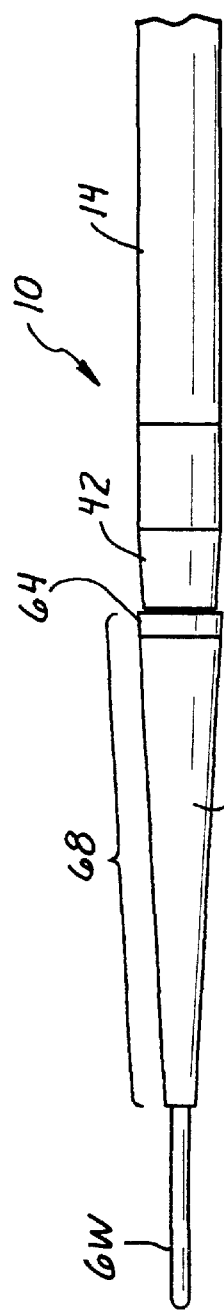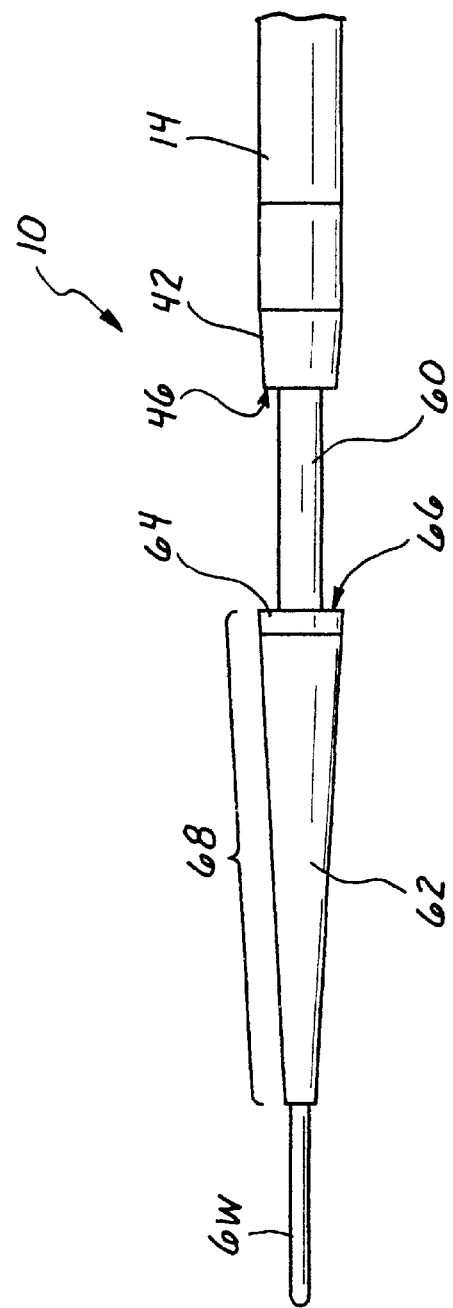

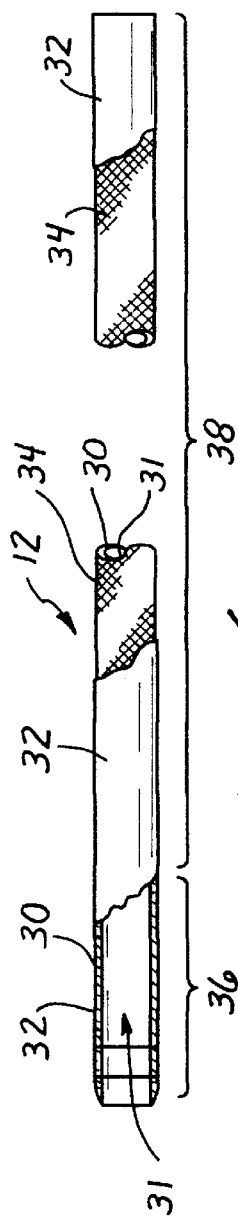
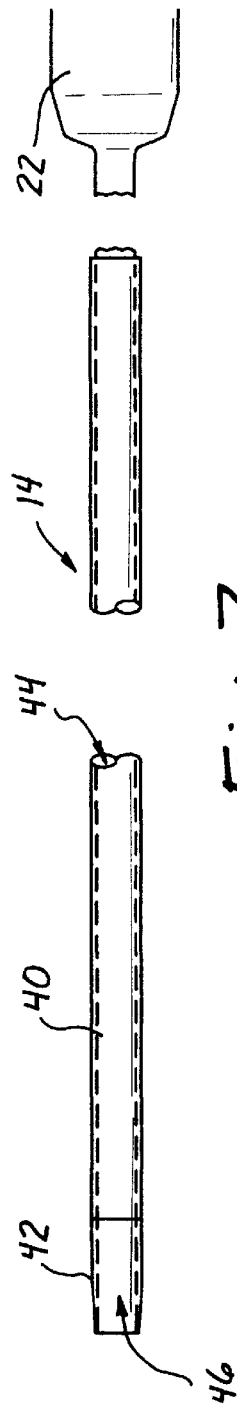
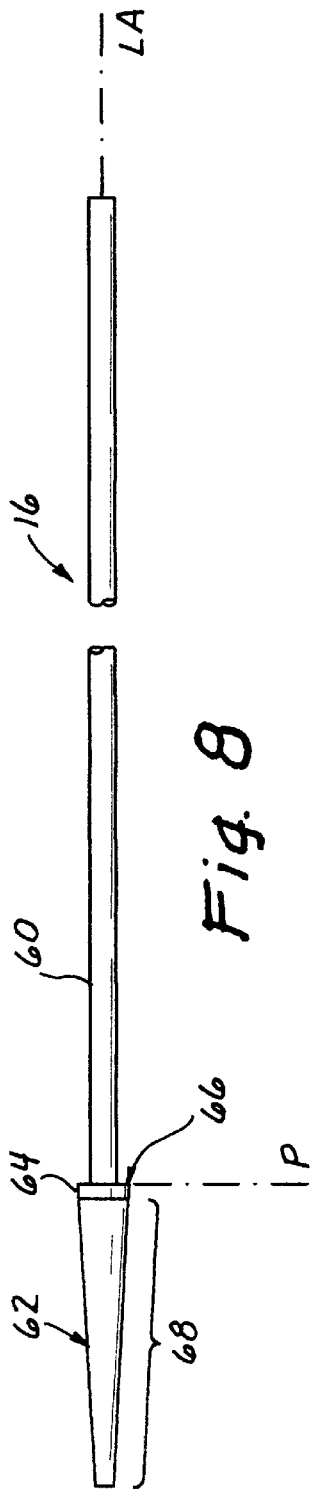
Fig. 6
Fig. 7
Fig. 8

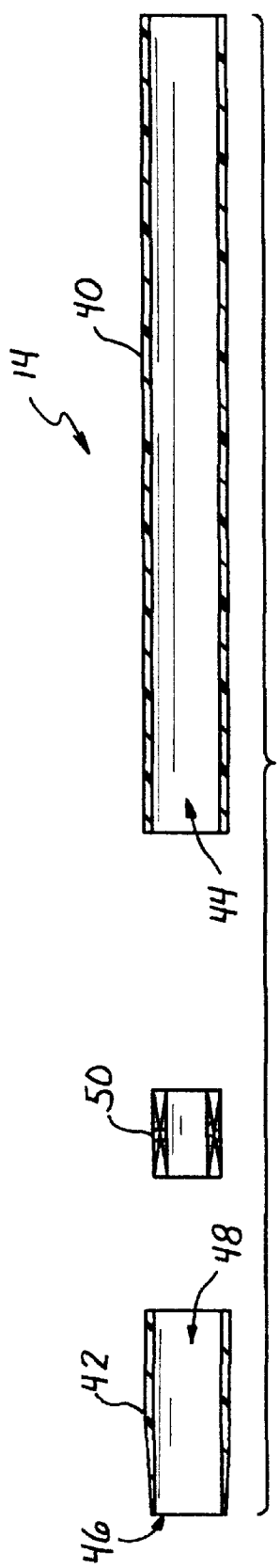
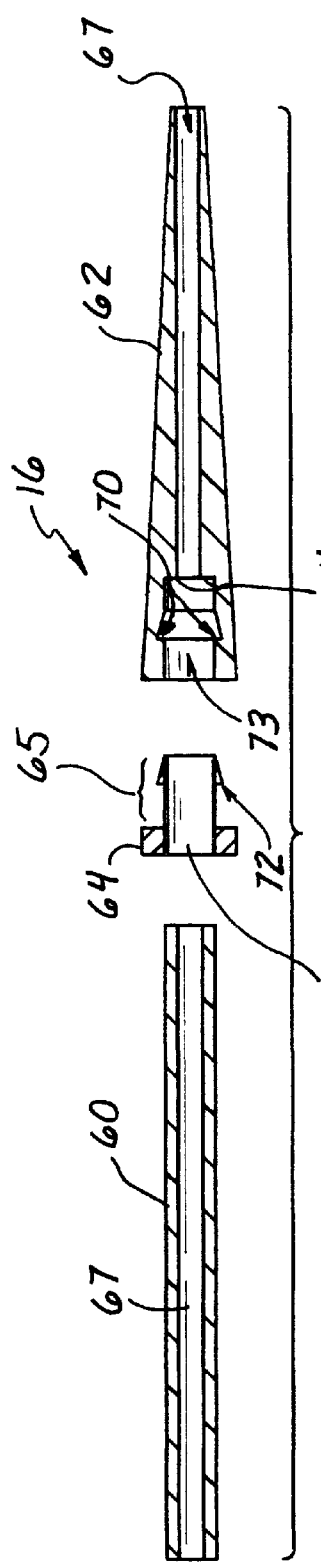

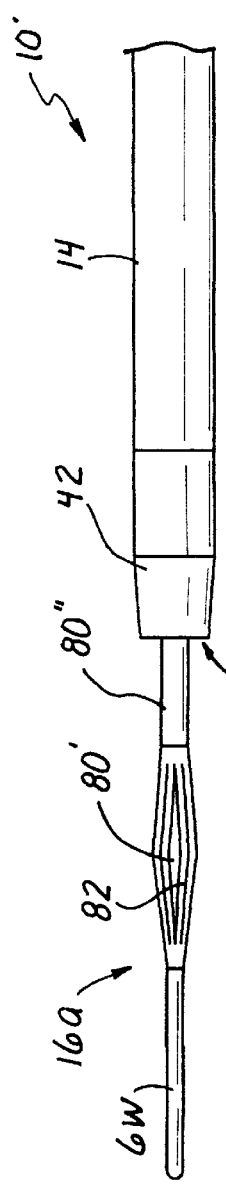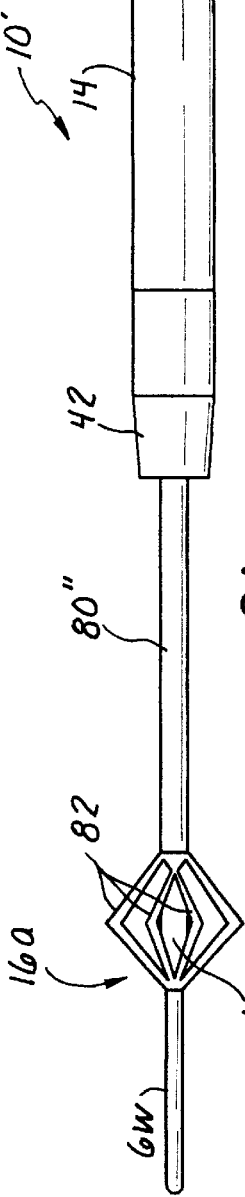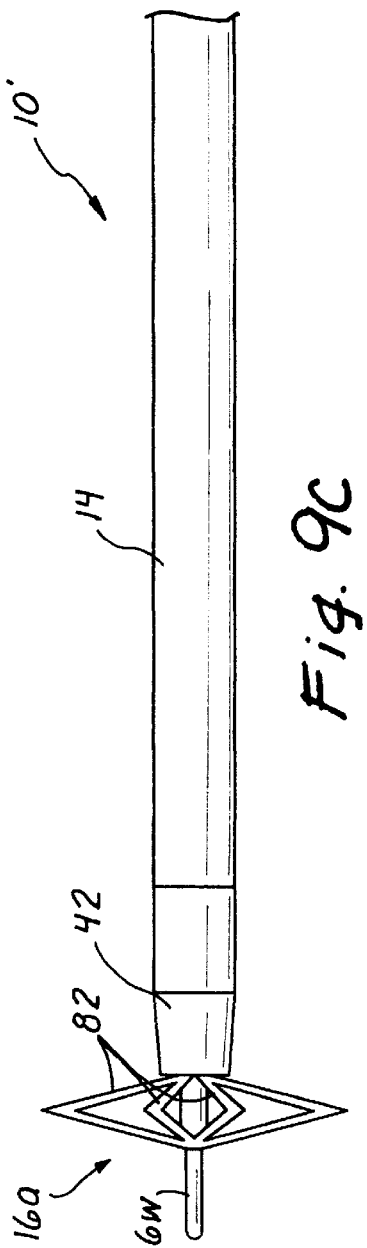

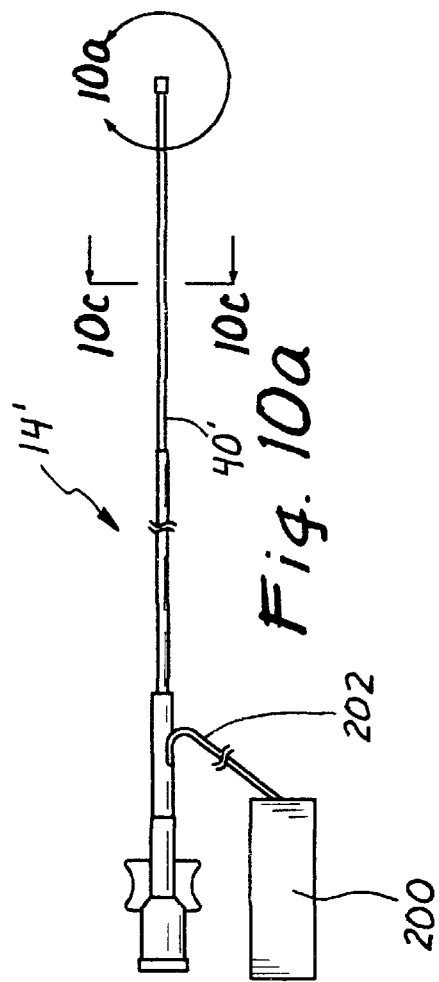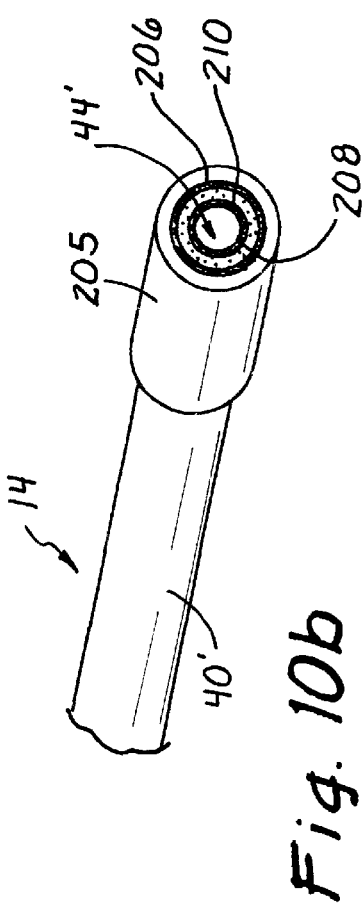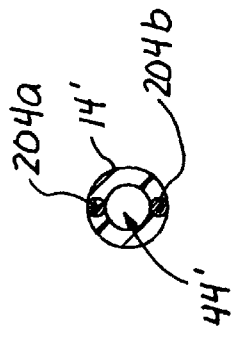

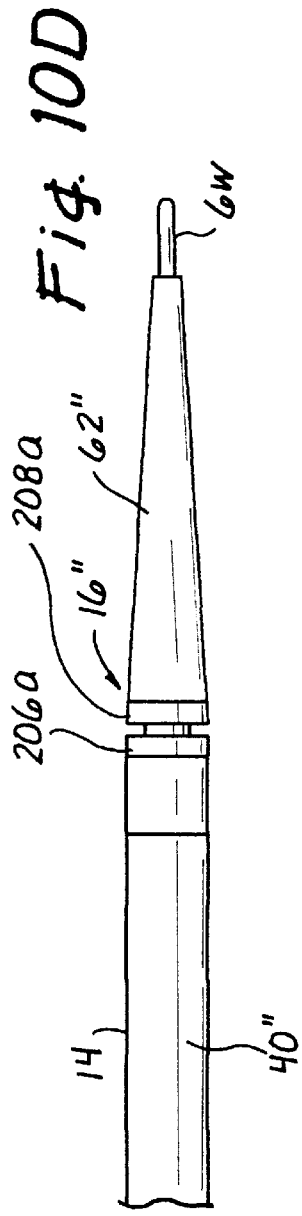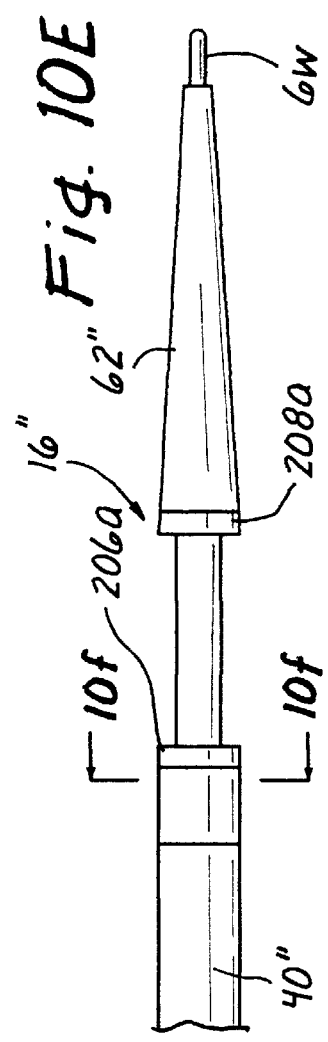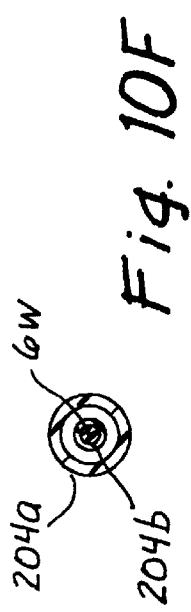

Fig. 10g 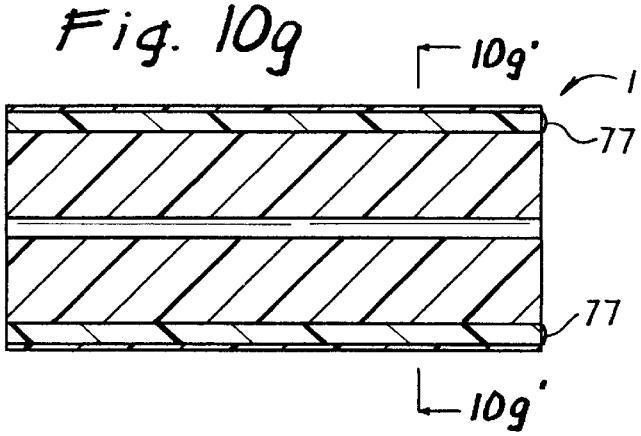 Fig. 10g' 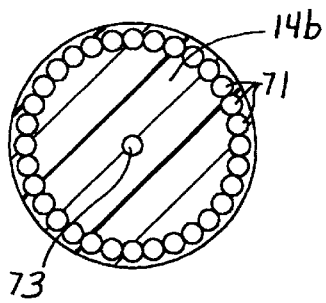

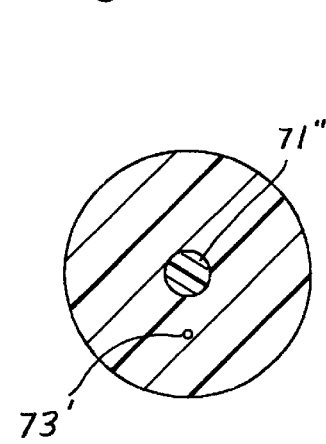
Fig. 10h'
Fig. 10i 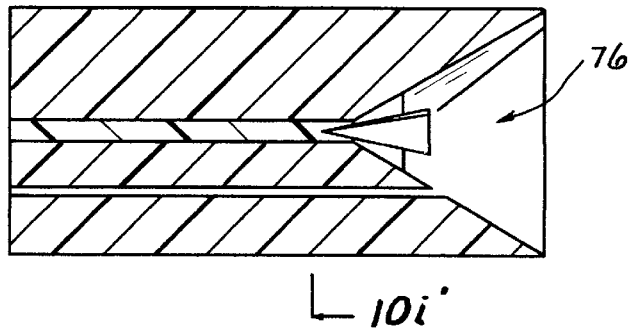 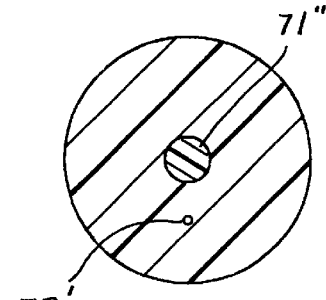 Fig. 10i'

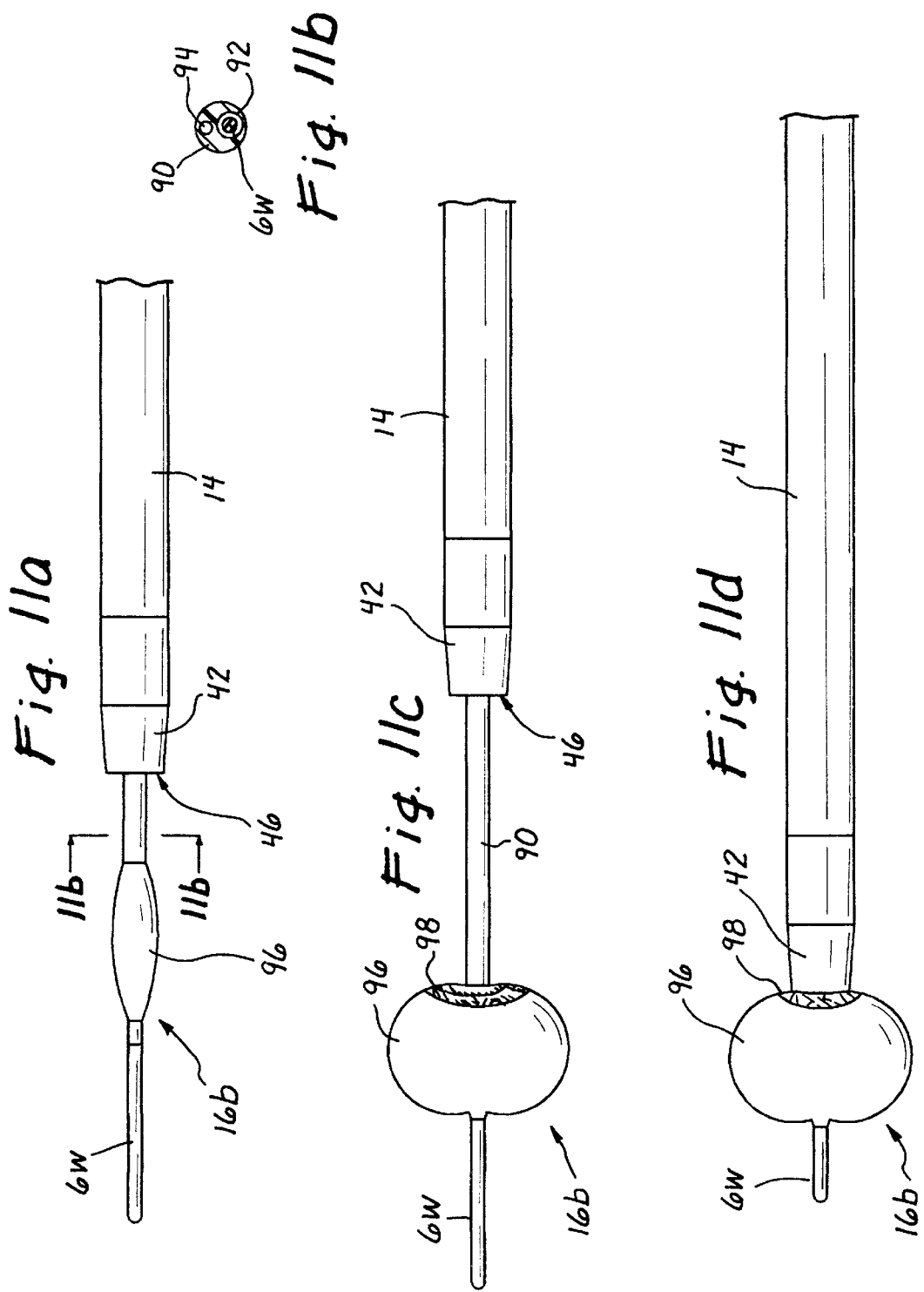

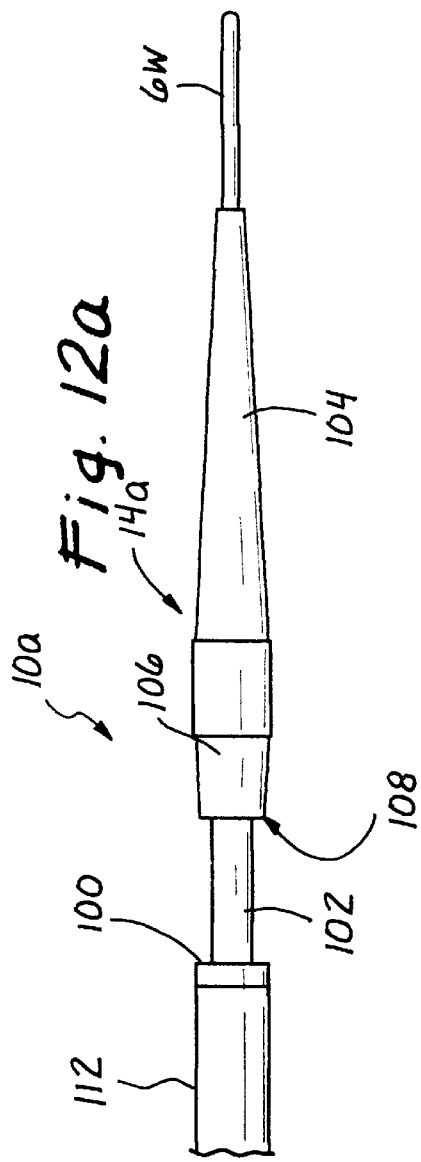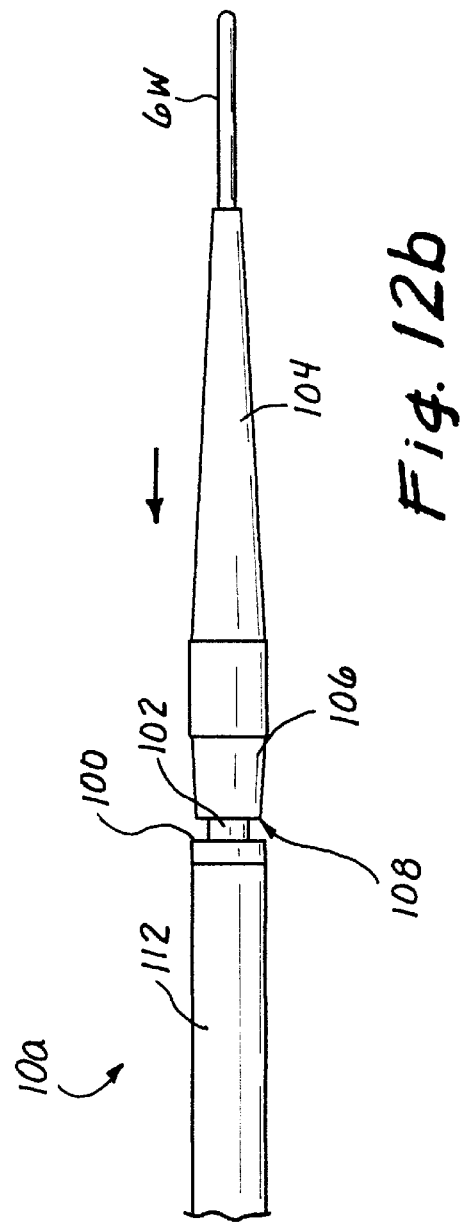

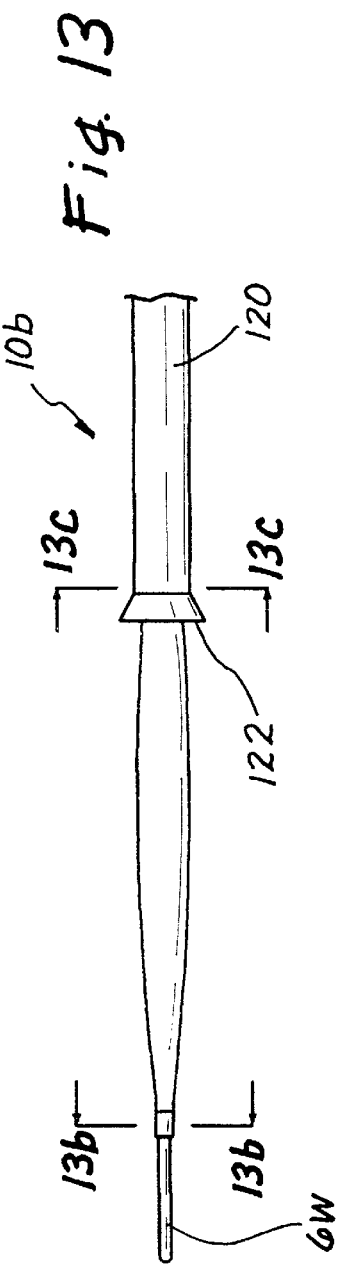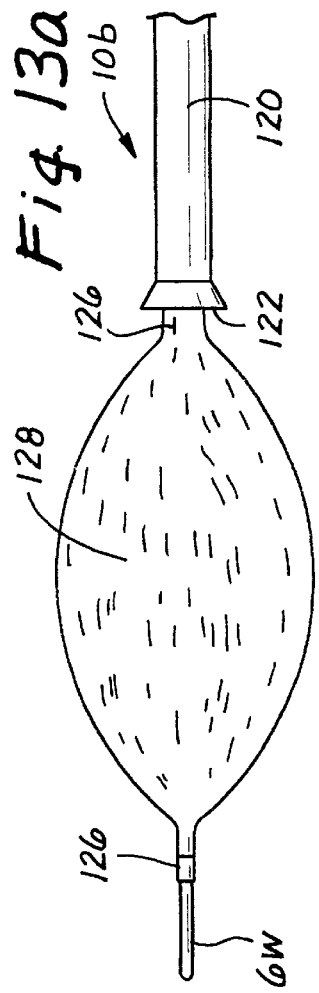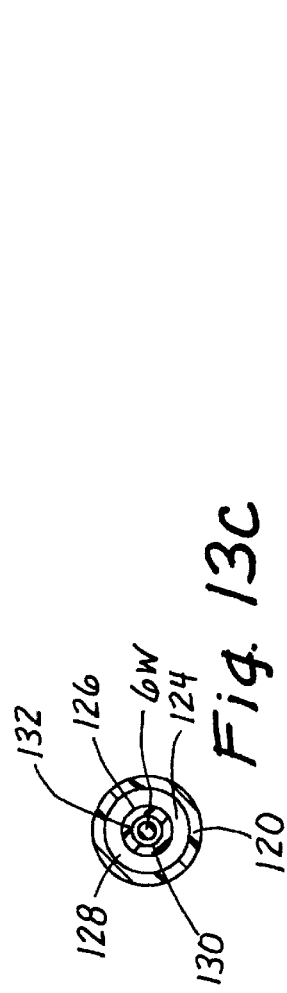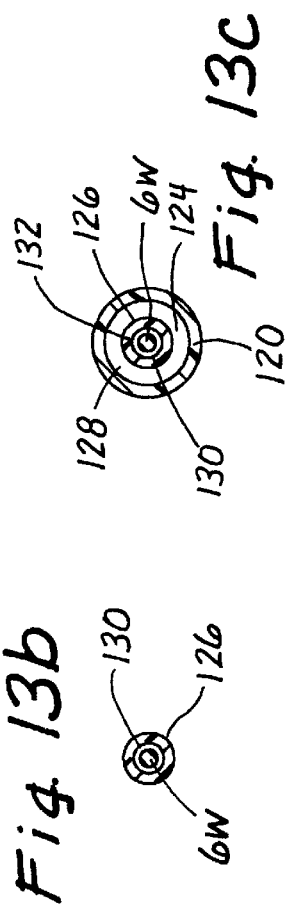

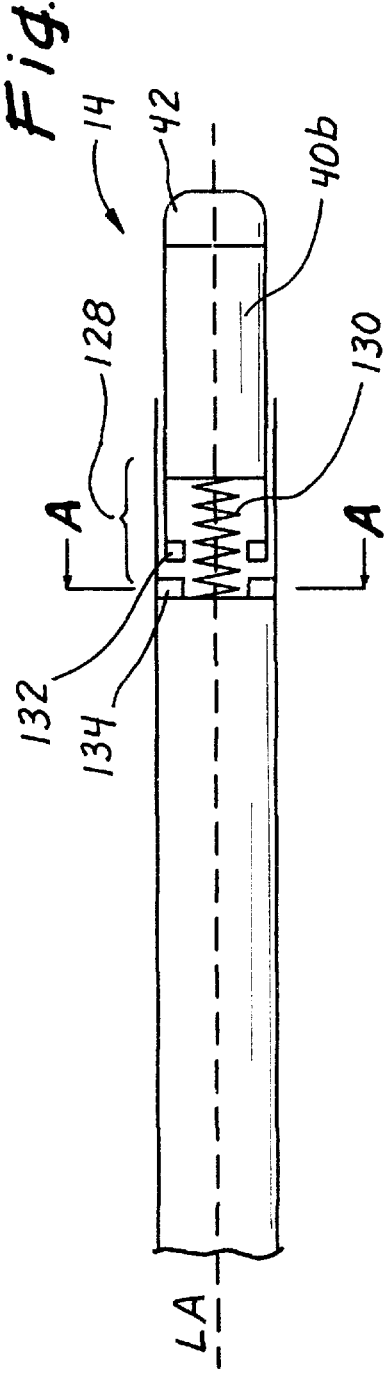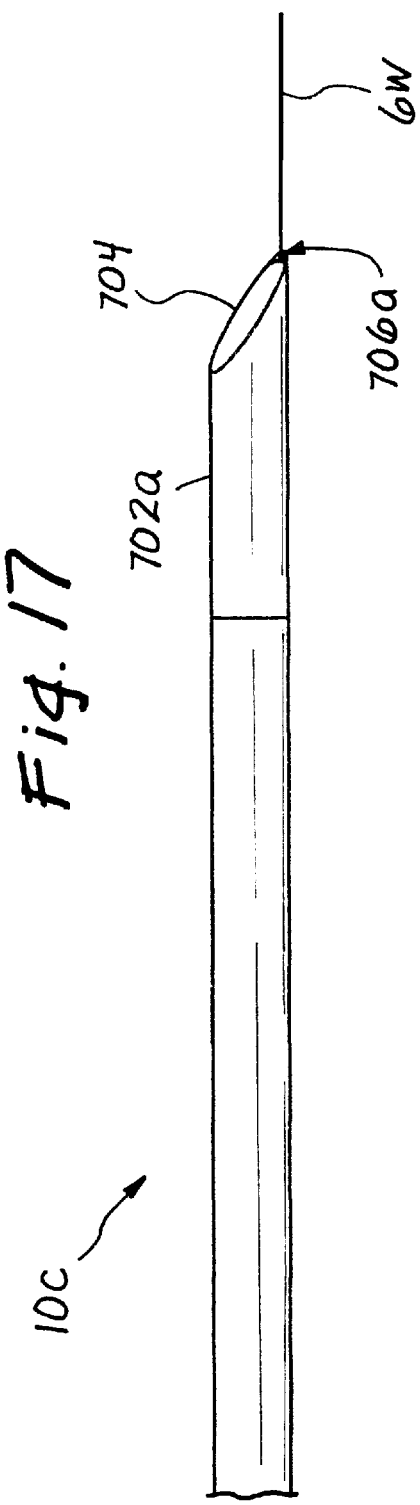

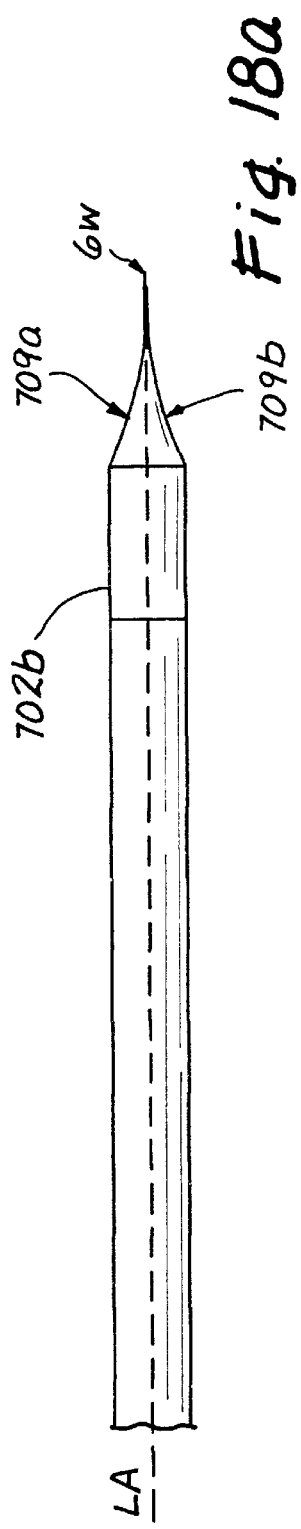
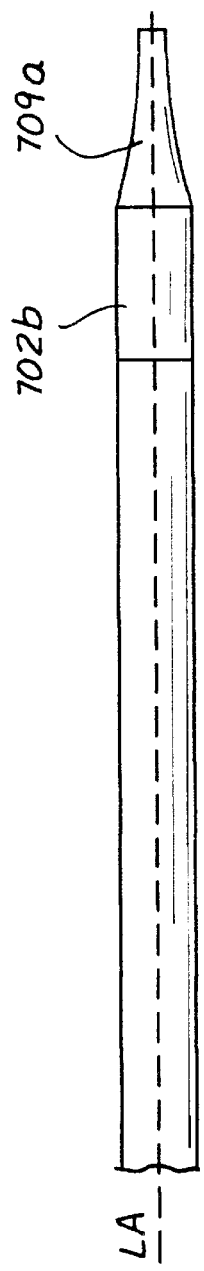
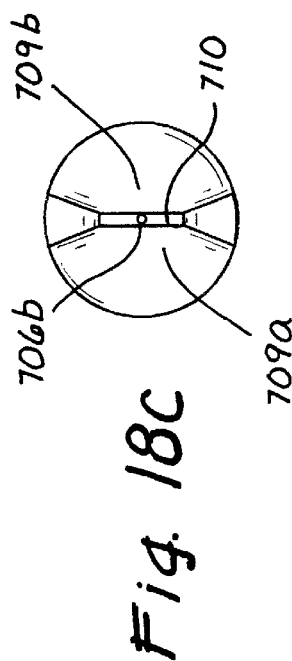

though of US 6,561,998 B1

TRANSLUMINAL DEVICES, SYSTEMS AND METHODS FOR ENLARGING INTERSTITIAL PENETRATION TRACTS

FIELD OF THE INVENTION

The present invention relates generally to medical devices and methods, and more specifically to transluminal devices, systems and methods which are useable to enlarge interstitial tracts (e.g., man made puncture tracts or small passageways) which extend between two (2) anatomical conduits (e.g., blood vessels) or otherwise through tissue(s) within a mammalian body.

BACKGROUND OF THE INVENTION

Applicant has devised several new medical procedures wherein passageway-forming catheters are advanced into anatomical conduits (e.g., blood vessels) and are used to create one or more interstitial passageways which extend outwardly, from the conduit in which the catheter is positioned, to another conduit or anatomical structure. Some of these procedures may be used to form flow-through passageways between the anatomical conduit (e.g., blood vessel) in which the passageway-forming catheter is positioned, and another anatomical conduit (e.g., another blood vessel) or a different location on the same anatomical conduit (e.g., a downstream site on the same blood vessel). Alternatively, these procedures may be used to form access passageways between the anatomical conduit (e.g., blood vessel, urethra, fallopian tube, etc.) and another anatomical structure (e.g., a tumor, organ, muscle, nerve, etc.).

In at least some of applicant's procedures, the interstitial passageway(s) are initially formed by advancing a tissue-penetrating element (e.g., a small diameter needle or a flow of tissue-penetrating energy) from the passageway-forming catheter, through the wall of the anatomical conduit in which the catheter is positioned, and into the target location. In some cases, the interstitial passageway which is formed by the initial passage of the tissue-penetration element from the passageway-forming catheter is of relatively small diameter- and must subsequently be enlarged (e.g., debulked, dilated, expanded, stretched) to accommodate the desired flow of biological fluid (e.g., blood) or passage of other substances/ devices therethrough.

In particular, as described in applicant's earlier-filed U.S. patent applications Ser. Nos. 08/730,327 and 08/730,496, such enlargement of the initially formed interstitial passageway (e.g., penetration tract) may be particularly important when the procedure is being performed to by-pass an obstruction within a coronary artery. For example, in some of applicant's procedures, a primary interstitial passageway is formed between an obstructed coronary artery and an adjacent coronary vein, such that blood will flow from the obstructed artery into the adjacent coronary vein. In such applications, the arterial blood which enters the adjacent coronary vein through the primary interstitial passageway is allowed to retroperfuse the ischemic myocardium by retrograde flow through the coronary vein. In other of applicant's procedures, one or more secondary interstitial passageways are formed between the coronary vein into which the arterial blood has flowed and the obstructed artery (or some other coronary artery) to allow arterial blood which has entered the coronary vein to reenter the obstructed artery (or some other coronary artery), after having bypassed the arterial obstruction. Thus, in either of these interventional procedures, it is important that the primary and/or secondary interstitial passageway(s) remain patent and sufficiently large in diameter to support the continued flow of arterial blood to the myocardium. However, the task of enlarging the small diameter interstitial passageway(s) (e.g., puncture tracts) formed by the initial passage of the tissue-penetrating element presents numerous technical challenges.

The prior art has included a number of catheter-based devices which may be used to enlarge or remove obstructive matter from the lumen of a blood vessel or other anatomical conduit (e.g., a blood vessel). These devices include; atherectomy catheters, embolectomy catheters, balloon angioplasty catheters, laser ablation catheters, etc. However, these prior art lumen-enlarging/lumen-clearing devices have typically not been intended for use in small diameter puncture tracts which diverge at an angle from the conduit lumen in which the catheter is located, as is typically the case in applicant's above-summarized interventional procedures.

Accordingly, there exists a need for the design and development of a new device, system and method for enlarging interstitial penetration tracts (e.g., man-made punctures or small passageways) which extend between adjacent anatomical conduits (e.g., blood vessels) within a mammalian body.

SUMMARY OF THE INVENTION

The present invention provides devices which are useable in combination with each other (i.e., as a system) to enlarge an interstitial tract (e.g., a small diameter penetration tract through tissue) which extends from a blood vessel or other anatomical conduit of the body. The tract enlarging systems of the present invention generally fall into three (3) major classifications—1) debulking-type systems, 2) dilating-type systems, 3) slicing-type systems and 4) two-catheter systems.

In accordance with the invention, one debulking-type tract enlargement system (referred to herein as an "advance-able" debulker) generally comprises: a) an elongate, pliable, tubular sheath sized for insertion into the lumen of an anatomical conduit from which the interstitial tract extends, said sheath having a lumen which extends longitudinally therethrough; b) a counter-traction member which is advanceable, i.) through the lumen of the tubular sheath and ii.) at least partially through the interstitial tract, such that the countertraction member engages or becomes positioned in relation to tissue which lies adjacent the interstitial tract to thereafter exert proximally-directed force upon such tissue; and, c) a debulker'(e.g., a tissue removing apparatus or flow of energy) which is advanceable out of the lumen of the sheath in a distal direction (i.e., substantially opposite the proximally-directed force being exerted by the counter-traction member) to remove tissue from the area adjacent the tract.

Further in accordance with the invention, there is provided another debulking-type tract enlargement system (referred to herein as a "retractable" debulker) generally comprises: a) an elongate, pliable, tubular sheath sized for insertion into the lumen of an anatomical conduit from which the interstitial tract extends, said sheath having a lumen which extends longitudinally therethrough, and b) a pull-back debulker (e.g., a tissue-removing apparatus or flow of energy) which is i.) initially advanceable out of the lumen of the sheath in a distal direction so as to pass through the penetration tract which is to be enlarged, and ii.) thereafter retractable in the proximal direction so as to remove, tissue which lies adjacent the interstitial tract, thereby enlarging the interstitial tract.

Still further in accordance with the invention, there is provided a dilating-type tract enlargement system (referred to herein as a "dilating" system) which generally comprises: a) an elongate, pliable, tubular sheath sized for insertion into the lumen of an anatomical conduit from which the interstitial tract extends, said sheath having a lumen which extends longitudinally therethrough, and b) a dilator (e.g., an elongate member) having at least one tissue-dilating member (e.g., a tapered, frusto-conical member, balloon or radial deployable member(s)) formed thereon, such dilator being advanceable into the penetration tract which is to be enlarged, and is subsequently useable to dilate such penetration tract, thereby resulting in the desired enlargement thereof. A positioning surface may be formed on the dilator to abut against tissue which lies adjacent the passageway in a manner which will enable the operator to determine that the dilator has been advanced to its desired position and is properly located to allow the dilate the interstitial tract as desired.

Still further in accordance with the invention, there is provided a slicing-type tract enlargement system (referred to herein as a "tissue-slicing" system) which generally comprises a) an elongate shaft which is advanceable through the interstitial tract, and b) at least one tissue slicing member which extends or is extendable from the shaft to incise or cut tissue which lies adjacent the interstitial tract as the shaft is advanced and/or retracted through the tract. In some embodiments, the tissue slicing member(s) may be initially disposed in a radially compact configuration which is flush with, or only slightly protrusive beyond, the outer surface of the shaft, thereby allowing the shaft to be advanced through the interstitial tract without cutting or disrupting the surrounding tissue. Thereafter, the tissue slicing member(s) is/are shifted to a radially expanded configuration wherein such tissue-slicing member(s) extend or protrude laterally from the shaft so as to slice, incise or cut at least some of the tissue which surrounds the tract. The tissue-slicing member (s) need not be concentric about the shaft, but rather may be of substantially flat configuration so as to create a defined incision or cut in the tissue. Moreover, the tissue-slicing member(s) may be configured so as not to completely sever and remove tissue in the manner of the above-summarized debulking-type embodiment, but rather may simply form a lit or incision adjacent the tract such that the surrounding tissue will continuously or intermittently separate to allow flow of fluid (e.g., blood) therethrough.

Still further in accordance with the invention, there is provided a two-catheter type tract enlarging system (referred to herein as a "two-catheter" system) which is specifically useable to enlarge an interstitial tract or passageway which has been formed between two adjacent anatomical conduits (e.g., blood vessels). Such two-catheter system generally comprises a) a first catheter having a tract-enlarging apparatus (e.g., a debulker, dialtor or tissue-slicing member of the above-described nature) which is advanceable from an opening at or near the distal end of that catheter, and b) a second catheter which has an anvil member (e.g., an abuttable surface or receiving cavity) which is sized and configured to correspond with the leading end of the tract-enlarging apparatus of the first catheter. The first catheter is positioned in one of the anatomical conduits, and the second catheter is positioned in the other anatomical conduit, with its anvil member located next to the interstitial tract or passageway which is to be enlarged. Thereafter, the tract enlarging, apparatus is advanced through the tract or passageway until it registers with (e.g., abuts against or is received with) the anvil member of the second catheter. As the tract enlarging apparatus is being advanced, the anvil member serves to provide counterforce against the tissue adjacent the initially formed tract or passageway so as to prevent unwanted protrusion or "tenting" of the tissue into the second anatomical conduit, and to ensure efficient cutting of the tissue in cases where a debulking or tissue slicing type tract enlarging apparatus is used.

Still further in accordance with the invention, either the debulking-type, dilating type, tissue-slicing type or two catheter type tract enlargement systems of the present invention may incorporate a guidewire lumen which extends longitudinally through the i.) tract enlarging member (e.g., debulker, dilator or tissue slicing member) to permit the tract enlarging member to be advanced over a small guidewire which has previously been passed through the penetration tract which is to be enlarged. Thus, the provision of such guidewire lumen may permit the system to be used to dilate penetration tracts which are of extremely small diameter, or which have become substantially closed off due to constriction of the surrounding tissue, provided that a guidewire was previously inserted through such penetration tract.

Still further in accordance with the invention, energy such as radio-frequency energy or electrical resistance heat may be applied to the tract enlarging member (e.g., debulker, dilator, or tissue slicing member) to enhance the tract-enlarging efficiency thereof.

Still further objects and advantages of the present invention will become apparent to those of skill in the relevant art, upon reading and understanding of the following detailed description of the invention and the accompanying drawings.

BRIEF DESCRIPTION OF THE DRAWINGS

FIG. 3 is an enlarged sectional view through line 3—3 of FIG. 2a.

FIG. 4 is an enlarged, side elevational view of the distal portion of the tract enlarging system of FIG. 1.

FIG. 4a is a cross sectional view through line 4a—4a of FIG. 4.

FIG. 4b is a cross sectional view through line 4b—4b of FIG. 4.

FIG. 4c is a cross sectional view through line 4c—4c of FIG. 4.

FIG. 5a is a side elevational view of the distal portion of the tract enlarging system of FIG. 1 disposed in a retracted configuration.

FIG. 5b is a side elevational view of the distal portion of the tract enlarging system of FIG. 1 disposed in a retracted configuration.

FIG. 6 is a is a longitudinal sectional view of the distal portion of the subselective sheath component of the system of FIG. 1.

FIG. 7 is a is a longitudinal sectional view of the distal portion of the tissue cutter component of the system of FIG. 1.

FIG. 7a is an exploded, longitudinal sectional view of the distal potion of the tissue cutter of FIG. 7.

FIG. 8 is a side elevational view of the counter-traction member component of the system of FIG. 1.

FIG. 8a is an exploded, longitudinal sectional view of the distal potion of the counter-traction member of FIG. 8.

FIG. 9a shows a first alternative counter-traction member having a tissue-engaging member formed of radially expandable members, wherein the radially expandable members are in their collapsed configuration.

FIG. 9b shows the first alternative counter-traction member of FIG. 9a, with its radially expandable members in a partially expanded configuration.

FIG. 9c shows the first alternative counter-traction member of FIG. 9a, with its radially expandable members in their fully expanded configuration.

FIG. 10a is a side elevational view of a debulking-type tract enlarging system which is equipped with a first type of an energy emitting debulker (e.g., a radio-frequency system).

FIG. 10b is an enlarged perspective view in the distal end of the energy emitting debulker of FIG. 10.

FIG. 10c is a cross sectional view through line 10c—10c of FIG. 10a.

FIG. 10d is a side elevational view of the distal portion of an another alternative debulking-type system which comprises an energy-emitting debulker in conjunction with an energy emitting counter-traction member, and wherein the energy emitting counter-traction member is in a retracted position.

FIG. 10e shows the system of FIG. 10c with its energy-emitting countertraction member in its extended position.

FIG. 10f is a cross sectional view through line 10e—10e of FIG. 10d.

FIG. 10g is a partial side elevational view of another energy-emitting debulker which incorporates an annular array of laser-transmitting optical fibers.

FIG. 10g' is a cross-sectional view through line 10g'—10g' of FIG. 10g.

FIG. 10h' is a cross-sectional view through line 10h'—10h' of FIG. 10h.

FIG. 10i is a partial side elevational view of another energy-emitting debulker having a rotatable laser-transmitting optical fiber (or fiber bundle) and a frusto-conical prism which projects a single ray of laser light but which, when rotated, will form a generally conical laser light pattern.

FIG. 10i' is a cross-sectional view through line 10i'—10i' of FIG. 10i.

FIG. 11a shows a debulking-type tract enlarging system having a second alternative counter-traction member which comprises an inflatable tissue-engaging balloon, wherein the balloon is in its non-inflated, collapsed configuration.

FIG. 11b is a cross sectional view through line 11b—11b of FIG. 11a.

FIG. 11c shows the second alternative counter-traction member of FIG. 11a, with its balloon in a fully inflated, expanded configuration.

FIG. 11d shows the second alternative countertraction member of FIG. 11a, with its balloon in its fully inflated, expanded configuration and the shaft fully retracted into the lumen of the debulker.

FIG. 12a is a side elevational view of the distal portion of a retractable debulking-type tract enlarging system of the present invention, wherein the retractable debulker is disposed in a distally extended position.

FIG. 12b is a view of the system of FIG. 12A, wherein the debulker is disposed in a partially retracted position.

FIG. 13 is a side elevational view of a dilation-type tract enlarging system of the present invention, disposed with its dilator (i.e. balloon) in a stowed (i.e., deflated) position.

FIG. 13a is view of the system of FIG. 13, disposed with its dilator (i.e., balloon) in an operative (i.e., inflated) position.

FIG. 13b is a cross sectional view through line 13b—13b of FIG. 13. FIG. 13c is a cross sectional view through line 13c—13c of FIG. 13.

FIG. 16 is a longitudinal sectional view of the distal portion of a debulker of the present invention which incorporates an apparatus for controlling the pressure applied by the debulker and/or for signifying when the debulking procedure is complete.

FIG. 17 is a side elevational view of the distal portion of a tissue-cutting type of tract enlarging system of the present invention.

FIG. 18a is a side elevational view of an alternative tissue-cutting tip for the system of FIG. 17.

FIG. 18b is a top plan view of the alternative tissue-cutting tip of FIG. 18a.

FIG. 18c is a distal end view of the alternative tissue cutting tip of FIG. 18a.

DETAILED DESCRIPTION OF THE PREFERRED EMBODIMENTS

Figure 1:
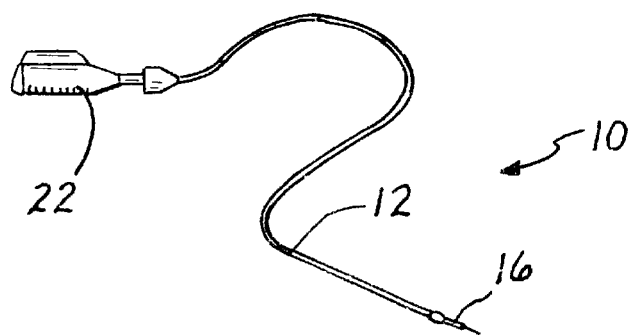
FIG. 1 is a perspective view of a debulking-type tract enlarging system of the present invention.
Figure 2:
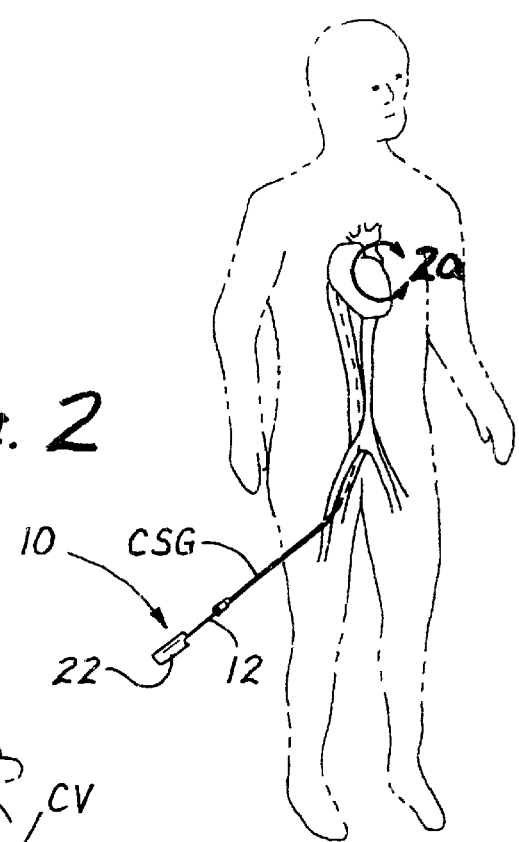
FIG. 2 is a schematic perspective view of a human body having the tract enlarging system of FIG. 1 operatively inserted into the coronary vasculature.
Figure 2A:
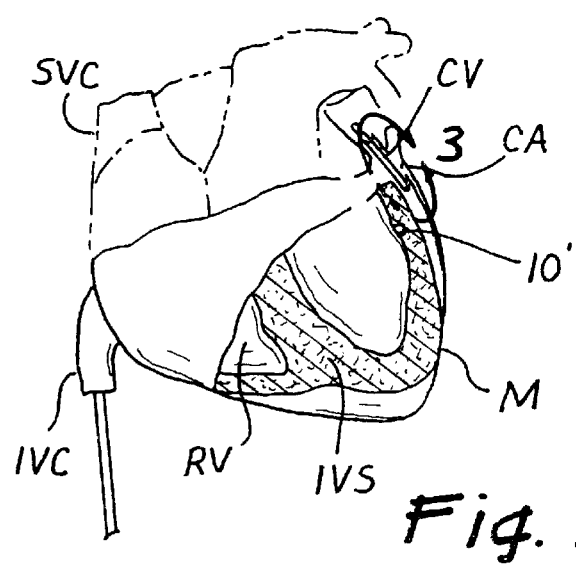
FIG. 2a is an enlarged, cut-away view of segment 2a—2a of FIG. 2.

The preferred embodiments and examples described in the following paragraphs, and shown in the accompanying drawings, should be considered as exemplars, rather than limitations on the devices, systems and methods of the present invention.

The particular embodiments described in detail below include debulking-type tract enlarging systems 10 and 10a, dilating-type tract enlargement systems 10b, and tissue-slicing-type tract enlarging systems 10c.

A. Debulking-Type Systems

Generally, the debulking-type systems 10, 10a serve to remove (e.g., cut, sever, ablate, vaporize, etc.) tissue which surrounds or lies adjacent to the initially formed interstitial tract thereby enlarging the tract. The description set forth in the following paragraphs includes a distally advanceable debulking-type system 10 as well as a proximally retractable debulking-type system 10a.

1. Advanceable Debulking-Type Systems

FIGS. 1–9 show a preferred, distally-advanceable debulking-type tract enlarging system 10 which is useable to enlarge a penetration tract. As shown in detail in FIGS. 4–8a, this distally advanceable debulking system 10 generally comprises a) a subselective sheath 12, b) a distally-advanceable debulker 14 which is passable out of the subselective sheath, in a distal direction DD, and a counter-traction member 16 which is advanceable through the penetration tract ahead of the debulker 14, and engageable with tissue adjacent the tract to exert a counter-force (i.e. a force directed in the proximal direction PD) upon the tissue which is to be severed by the distally advancing debulker 14. It is also to be understood that the counter-traction member 16 may similarly be positioned adjacent the tissue such that it does not actually exert force against the tissue until the debulker 14 is advanced into contact with the tissue, at which time the tissue will then be compressed between the debulker and the counter-traction member 16 as the debulking procedure is performed.

Subselective Sheath

The subselective sheath 12 of the embodiment shown in the drawings comprises a flexible tube which is sized to be advanceable into the anatomical conduit from which the interstitial penetration tract extends. With particular reference to the showings of FIGS. 4, 4c and 6, the preferred subselective sheath 12 comprises inner wall 30 preferably formed of formed of polytetrafluoroethylene (PTFE), an outer wall 32 preferably formed of polyether block amide polymer (e.g., Pebax™), and a braid 34 captured between inner 30 and outer 32 walls, such braid 34 terminating distally at a location which is approximately 2–10 mm from the distal end of the sheath 12. In this manner, there is defined a non-braided distal portion 36 of approximately 2–10 mm and a braided proximal portion 38. The presence of the braid 34 within the proximal portion 38 of the sheath 12 enhances its strength and resistance to crimping or kinking, while the non-braided distal portion 36 of the sheath 12 remains soft and pliable to avoid injury or damage to the walls of blood vessels or other tissues, as the sheath 12 is advanced. For use in coronary blood vessels, the sheath 12 will preferably have an outer diameter of 0.050–0.150 inch and an inner lumen diameter of 0.040–0.140 inch.

In some embodiments, the subselective sheath 12 may have lumen which curves laterally and exits through an outlet port formed in the sidewall of the sheath 12. Such side outlet sheath (not shown) may be advanced to a position where the side outlet aperture is in direct alignment with the penetration tract PT, and thereafter, the debulker 14 may be advanced out of the side outlet aperture and through the penetration tract PT.

Advanceable Debulker

One type of debulker 14 comprises a rotating tissue cutter which, when advanced in the distal direction and concurrently rotated, will sever and remove a cylindrical mass of tissue from the region surrounding the penetration tract. With particular reference to the showings of FIGS. 7 and 7a, this preferred debulker 14 comprises a flexible tube 40 which has a lumen 44 extending longitudinally therethrough, and an annular cutting member 42 mounted on the distal end thereof. The annular cutting member 42 has a sharpened leading edge 46 and a hollow bore 48 which extends therethrough. The cutting member 42 is mounted securely on the distal end of the tube, preferably such that the bore 46 of the annular cutting member 42 is in direct axial alignment with the lumen 44 of the tube 40, and the outer surface of the cutting member 42 is flush with the outer surface of the tube 40. The tube 40 is preferably formed of a flexible plastic (e.g., Pebax™ polyether block amide polymer). The cutter member 42 is preferably formed of a rigid material such as stainless steel. In embodiments intended for use in coronary blood vessels, this debulker 14 will preferably have an outer diameter of 0.05–0.13 inches and an inner (lumen) diameter of 0.04–0.12 inches. A plurality of bearing members 50 may be mounted at spaced-apart locations within the lumen 44 of the debulker 14 to facilitate rotation of the debulker 41 about a central shaft (e.g., the shaft 60 of the countertraction member 16). A drive motor/handpiece 22 may be mounted on the proximal end of the debulker 14, as shown in FIGS. 1 and 7. This drive motor/handpiece 22, when actuated, will rotationally drive the debulker 14, at a suitable rate of rotation to facilitate the desired severing of tissue. In applications where the debulker 14 is being used to sever soft tissue, it is preferable that the motor/handpeice 22 be capable of driving the debulker 14 at 60–300 revolutions per minute. One example of a commercially available drive motor/handpiece 22 which may be used is the MDV Motor Drive Unit manufactured by DVI, Inc.

Counter-traction Member

The counter-traction member 16 of the embodiment shown in the drawings serves to pass through the interstitial tract to be enlarged, ahead of the debulker, and prevents unwanted protrusion or "tenting" of the tissue into the adjacent anatomical conduit, thereby enhancing the tissue cutting efficiency of the debulker. With particular reference to the showings of FIGS. 4, 4a, 8 and 8a, the preferred counter-traction member 16 comprises an elongate, pliable shaft 60 having a dilator/tissue-engaging member 62 mounted on the distal end thereof, and a guidewire lumen 67. The tract dilator/tissue engaging member 62 comprises a frustoconical body 68 and a cutting-engagement plate 64 formed on the proximal end thereof. The proximal surface 66 of the cutting-engagement plate 64 is disposed in a plane P which is substantially perpendicular to the longitudinal axis LA of the shaft 60. The frustoconical portion is preferably formed of soft plastic such as polyether block amide polymer (e.g., Pebax™) and the cutting/engagement plate 64 is preferably formed of hard material such as polycarbonate or stainless steel. As shown in the exploded view of FIG. 8a, a cavity 73 may be formed in the proximal end of the dilator/engagement plate 62, including a shaft receiving portion 74 and an annular groove 70. The distal portion 65 of the cutter/engagement plate 64 is inserted into cavity 73 such that an annular shoulder 72 formed about the proximal portion 65 will frictionally engage a corresponding annular groove 70 formed about the interior of the cavity 73, thereby holding the cutting/engagement plate 64 in fixed position on the distal end of the dilator/engagement member 62. The distal end of the shaft 60 is then inserted through the bore 67 of the cutting/engagement plate 64 until it bottoms out in the shaft receiving portion 74 of the cavity 73. An adhesive or thermal compression bonding may be used to securely hold the shaft in contact with the dilator/engagement member 62. Additionally or alternatively, the proximal portion 65 of the cutting/engagement plate 64 may act as a ferrule, exerting radial inward pressure against the shaft to frictionally hold the shaft in its inserted position within the cavity. The counter-traction member 16 also acts to protect the adjacent vessel or luminal anatomical structure from iatrogenic trauma (e.g., perforation, laceration) as the debulker is advanced.

It is to be appreciated that various other types of tissue-engaging members may be utilized in addition to, or as an alternative to the particular counter-traction member 16 shown in FIGS. 1–8. Some examples of alternative types of countertraction members 16a, 16b, 16c are shown in FIGS. 9a–9c and 11a–11h.

With reference to FIGS. 9a–9c one alternative counter-traction member 16a comprises a telescoping shaft 80 formed of a distal shaft portion 80' and a proximal shaft portion 80", having a plurality of radially expandable members 82 disposed about the shaft 80, as shown. Preferably, a guidewire lumen (not shown) extends longitudinally through the shaft 80. Each radially expandable member 82 has a distal end which is affixed to the distal shaft portion 80' and a proximal end which is affixed to the proximal shaft portion 80". As shown in FIG. 9a, when the distal shaft portion 80' is fully advanced in the distal direction, the radially expandable members will be in a radially collapsed configuration of diameter D, which is sufficiently small to be advanceable through the previously formed penetration tract. Thereafter, as shown in FIGS. 9b and 9c, the distal shaft portion 80' may be retracted into the proximal shaft portion 80" to cause the radially expandable members to bow or expand outwardly. Thus, when the distal shaft portion 80' is partially retracted the radially expandable members 82 may assume a partially expanded configuration of diameter $D_2$ when the distal shaft member 80' is fully retracted the radially expandable members 82 will assume a fully expanded configuration of diameter $D_3$.

Referring to FIGS. 11a–11d, another alternative counter-traction member 16b comprises an elongate shaft 90 which has a guidewire lumen 92 and a balloon inflation/deflation lumen 94 extending therethrough, and a balloon 96 mounted thereon. With the balloon in its deflated state as shown in FIG. 10a, the shaft 90 is advanceable over a guidwire and through the penetration tract PT which is to be enlarged. After the balloon 96 has emerged out of the opposite end of the penetration tract PT, inflation fluid is injected through the inflation/deflation lumen 94 to inflate the balloon 96 as shown in FIG. 10c. As described in more detail herebelow, the inflated balloon 96 will the abut against and engage the tissue which surrounds the penetration tract PT, and will exert proximally directed force on such tissue while the debulker 14 is advanced through the tissue. As shown in FIG. 10d, after the tissue has been fully severed, the shaft 90 will be fully retracted into the lumen 44 of the debulker 14 and the cutting surface 46 of the annular cutting member 42 will abut against a reinforced region 98 of the balloon. Such reinforced region 98 is sufficiently resistant to cutting or puncture to prevent the annular cutting member 42 from bursting or penetrating through the wall of the balloon 96.

Figure 11E:
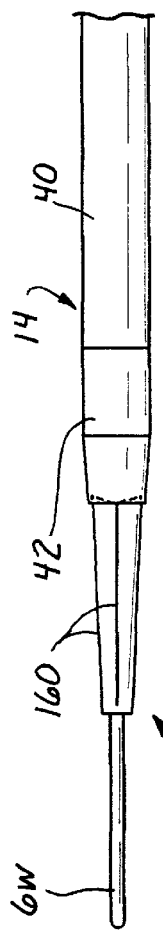
FIG. 11e shows a debulking-type tract enlarging system having an advanceable debulker and a third alternative counter-traction member comprising splayable tissue-engaging members, wherein the tissue-engaging members are in there radially collapsed, non-splayed configuration.
Figure 11F:
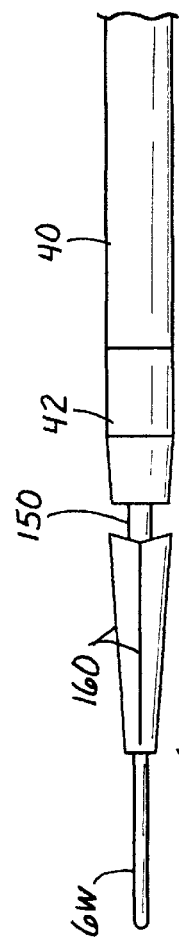
FIG. 11f shows the system of FIG. 11e with its tissue-engaging members in their splayed, radially expanded configuration.
Figure 11G:
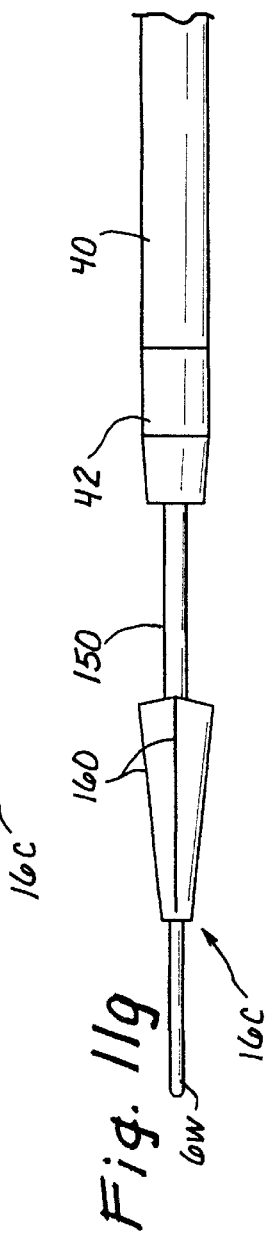
FIG. 11g shows the system of FIG. 11f with its counter-traction member is fully advanced out of the debulker.
Figure 11H:
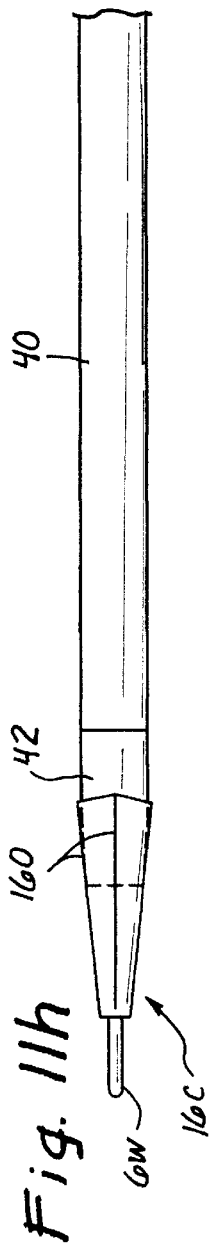
FIG. 11h shows the system of FIG. 11g wherein the tissue-engaging members are in their radially expanded configuration and the counter-traction member has been fully retracted such that the distal end of the debulker engages the interior of the expanded tissue-engaging members.

Referring to FIGS. 11e–11h, there is shown yet another counter-traction member 16c which comprises an elongate shaft 150 having a plurality of resilient or spring loaded, outwardly splayable members 160 which are attached at their distal ends to the shaft 150. The proximal ends of the splayable members 160 are biased to a radially expanded configuration as shown in FIGS. 11f–11h, but are initially compressible to a radially compact configuration wherein they may be received within the lumen 44 of the debulker, as shown in FIG. 11e. Initially, with the splayable members 160 are placed in their radially compact configuration and retracted at least partially within the lumen 44 of the tubular member 40 of the debulker 14. After the system has been inserted in the body and positioned adjacent the interstitial tract to be enlarged, the shaft 150 is advanced in the distal direction to drive the splayable members 160 through the interstitial tract. As the proximal ends of the splayable members emerge from the distal end of the interstitial tract, they will spring outwardly to their radially expanded configuration and will engage the tissue adjacent the distal end of the tract. Thereafter, proximally directed pressure may be applied to the shaft as the debulker 40 is advanced in the distal direction. This results in the desired counter-traction on the tissue being severed by the annular cutting member 42. At it end of the tract enlarging procedure, the leading edge 46 of the annular cutting member 42 will be nested within and in contact with the splayable members 160, as shown in FIG. 11h. In this manner, as will be more fully appreciated after reading the explanation of the detailed operation of the device set forth herebelow, the tissue which has been severed from the area surrounding the interstitial tract will be received within the lumen 44 of the debulker, for subsequent removal from the body.

Operation of the Distally Advanceable Debulking-type System

Prior to operation, the system 10 is assembled in the manner shown in FIG. 5a, such that the shaft 60 of the counter-traction member 16 is slidably and rotatably disposed within the lumen 44 of the debulker 14 (i.e. extending through the bearings 50 located within the lumen 44 of the debulker 14) and the countertraction member 16 and debulker 14 are positioned within the lumen 31 of the sheath 12. This system 10 may then be utilized to enlarge a small penetration tract PT which has been formed between an anatomical conduit and some other anatomical conduit or cavity within the body. For purposes of illustrating and explaining the operation of the present invention, FIGS. 3a–3d show a specific coronary revascularization procedure wherein an interstitial passageway is to be formed between a coronary vein CV and an adjacent coronary artery CA, to permit arterial blood to flow into the coronary vein CV.

Figure 3:
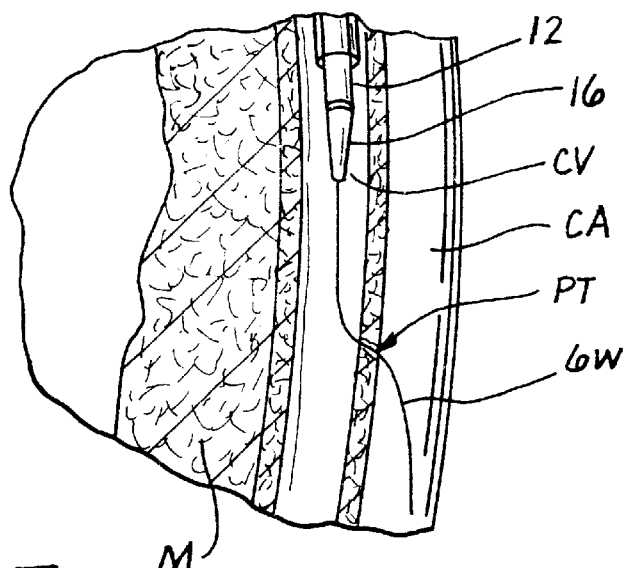
Figure 3A:
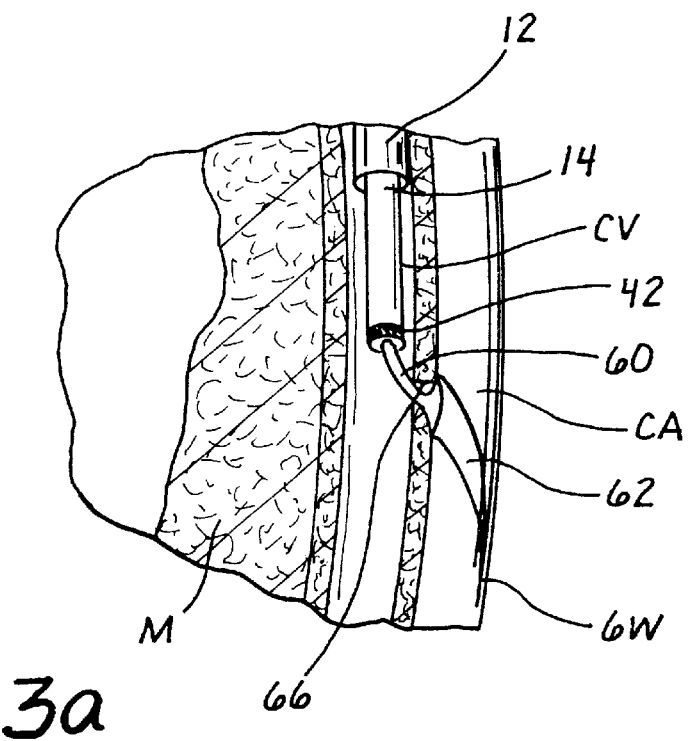
FIGS. 3a–3d are step-wise showings of a presently preferred method for using the tract enlarging system of FIG. 1 to debulk and enlarge an interstitial penetration tract which has been created between a coronary artery and an adjacent coronary vein.
Figure 3B:
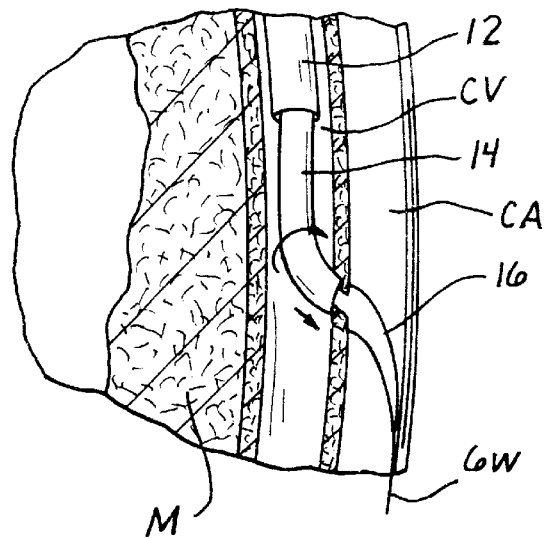
Figure 3C:
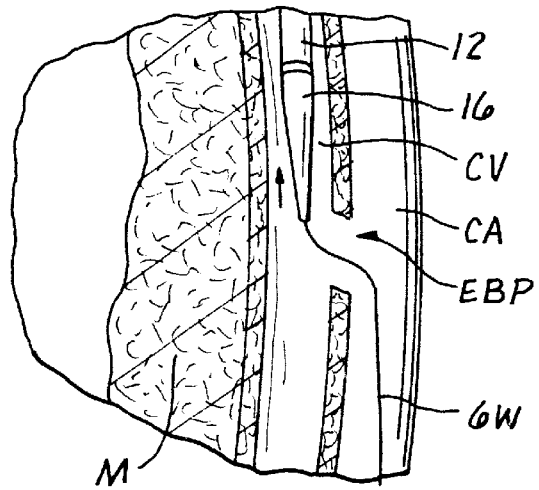

With reference to FIGS. 3a–3d, after an interstitial penetration tract PT has been formed between a coronary artery CA and coronary vein CV, a small guidewire GW is passed through such penetration tract PT. The guidewire GW is passed, proximal end first, into the distal end of the guidewire lumen 67 which extends through the counter-traction member 16. With the debulker 14 and countertraction member 16 disposed within the lumen 31 of the subselective sheath 12, the system 10 is advanced over the guidewire GW until the distal end of the subselective sheath 12 becomes positioned within the coronary vein CV at a location approximately 0.10 inch (i.e., 2–3 mm) from the penetration tract PT. Thereafter, as shown in FIG. 3, the counter-traction member is further advanced such that the dilator/engagement member 62 will pass through the penetration tract PT and into the coronary artery CA. As the dilator/engagement member emerges into the lumen of the coronary artery CA the tissue surrounding the penetration tract PT will elastically retract about the distal portion of the shaft and the proximal surface 66 of the cutting/engagement plate 64 will abut against the coronary artery wall immediately adjacent the opening of the penetration tract PT into the coronary artery CA. Thereafter, proximally directed pressure is applied to the counter-traction member 16 while concurrently advancing the debulker 14 in the distal direction, as shown in FIG. 3a. As the advancing debulker 14 comes into contact with the tissue which surrounds the penetration tract PT, the drive motor/handpiece 22 is actuated so as to rotate the debulker at approximately 60–300 RPM. As shown in FIG. 3b, this causes the sharpened leading edge 46 of the cutting member 42 to cut a cylindrical bolus of tissue as the rotating debulker 14 continues to advance. The application of proximally directed pressure on the counter-traction member 16 concurrently with the distally directed advancement of the debulker 14 prevents the surrounding tissue from "tenting" and enhances the cutting efficiency of the debulker 14. Also, because the tissue which is being severed is located directly behind the cutting/engagement plate 64, the severed bolus of tissue will be prevented from escaping into the coronary artery CA, and will be forced into the lumen of the debulker 14 whereby it may be extricated and removed from the body along with the debulker 14, as illustrated in FIG. 3c. This results in the formation of an enlarged bloodflow passageway EBP, as desired.

Figure 3D:
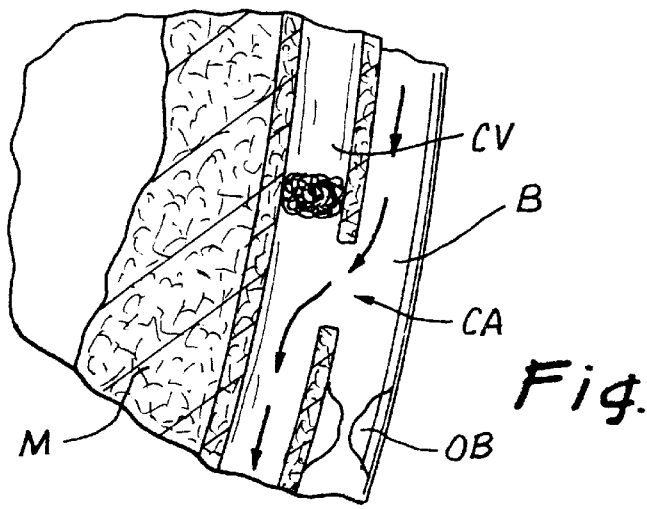

As shown in FIG. 3d, and in accordance with applicants methodology described in earlier-filed U.S. patent applications Ser. Nos. 08/730,327 and 08/730,496, one or more embolic blockers B or other flow-blocking means may be utilized to prevent arterial blood which enters the coronary vein CV through the enlarged bloodflow passageway EBP from flowing in the venous return direction, and to cause such arterial blood to flow through the coronary vein CV in the retrograde direction, thereby bypassing the obstruction OB located in the adjacent coronary artery CA.

2. Retractable Debulking-type Systems

FIGS. 12a–12b show an example of a retractable debulking-type tract enlargement system 10a, of the present invention. This system 10a comprises a proximal counter-force member 112 in combination with a retractable debulker 14a, as shown in FIGS. 12a and 12b.

Proximal Counter-force Member

The proximal counter-force member 112 comprises a tube having a lumen (not shown) which extends longitudinally therethrough and an annular cutting/engagement plate 100 formed on the distal end thereof. The annular cutting/engagement plate 100 serves to engage a pull-back tissue cutter formed on the proximal end of the retractable debulker 14a. In embodiments where the retractable debulker is rotatable, a plurality of bearings 50 of the type described hereabove may be coaxially disposed at spaced apart locations within the lumen of the proximal counter-force member 112.

Retractable Debulker

The retractable debulker 14a of this embodiment comprises a shaft 102 having a flexible frusto-conical dilator 104 formed thereon, and an annular cutter member 106 mounted on the proximal end of the dilator 104, as shown. The frusto-conical dilator 104 may be constructed and configured the same as the frustoconical body 68 described hereabove. The annular cutting member 106 may be constructed and configured the same as the annular cutting member 42 of the first embodiment described hereabove. This annular cutting member 106 has a sharpened proximal edge 108 which will sever tissue when retracted therethrough. A guidewire lumen(not shown) extends longitudinally through the shaft 102 and through the frusto-conical dilator. Optionally, the retractable debulker 14a may be rotatably driven by a drive motor/handpiece as described hereabove.

Operation of the Retractable Debulker Type System

Prior to operation, this retractable debulking type system 10a is assembled such that shaft 100 the retractable debulked 14a is slidably and (and in some cases rotatably) disposed within the lumen of the proximal counter-force member 112. In embodiments wherein the debulker 14a is rotatable, the shaft 102 will extend through any bearings 50 disposed within the lumen of the counter-force member 112. The shaft 102 may initially be retracted such that the proximal sharpened edge 108 of the annular cutter, 106 is in abutment with the annular cutting plate 100. The counter-force member 112 and retractable debulker 14a are positioned within the lumen 31 of a subselective sheath 12 as described hereabove. This system 10a may then be utilized to enlarge a small penetration tract PT which has been formed through the sidewall of and extending outwardly from an anatomical conduit of the body, and through which a guidewire has been inserted.

The guidewire GW which extends through the penetration tract is inserted into the distal end of the guidewire lumen (not shown) of the retractable debulker 14a. The subselective sheath 12 having the counterforce member 112 and retractable debulker positioned therewith, is maneuvered into the anatomical conduit from which the penetration tract extends. Thereafter, the shaft 102 of the retractable debulker 14a is advanced such that the dilator 104 is forced through the penetration tract. After the sharpened proximal edge 108 of the retractable debulker 14a has emerged out of the opposite end of the penetration tract, the tissue which surrounds the penetration tract will elastically constrict about the shaft. The counter-force member 112 is then advanced until the distal lo annular cutting plate 100 is in abutment with the wall of the portion of the wail of the anatomical conduit which surrounds the proximal end of the penetration tract.

Thereafter, distally directed counter-force is applied to the counter-force member 112 while the retractable debulker 14a is retracted in the proximal direction. Optionally, the retractable debulker 14a may be rotated concurrently with its retraction. As the debulker 14a is retracted, the sharpened proximal edge 108 of the annular cutting member 106 will sever a generally cylindrical bolus of tissue which surrounds the puncture tract, thereby accomplishing the desired enlargement of the initially formed penetration tract. The severed bolus of tissue will be drawn into, and captured within, the lumen (not shown) of the counter-force member 112 as the sharpened proximal edge 108 of the annular cutting member 106 is retracted into contact with the annular cutting plate 100.

Thereafter, the counter-force member 112 (having the severed bolus of tissue contained therewithin) and the retractable debulker 14a, may be removed from the body along with the subselective sheath 12.

3. Sizing and Shaping of the Debulker to Optimize Flow Channel

In either debulking type system 10, 10a the particular geometry of the cutter member 42 can assist in creation of the optimal passage, such as the enlarged bloodflow passageway EBP of the foregoing example. For example, the annular cutting member 42 need not be of circular cross-sectional configuration as shown in FIG. 7a, but rather may be of oblong or oval configuration. Such oblong or oval shape of the annular cutting member 42, when advanced through the puncture tract without rotation thereof, will form a channel of oval or oblong cross-sectional shape.

Also, as shown on FIG. 4, the annular cutting member 42 may be of tapered outer diameter, such that its distal cutting edge is of a first diameter $d_x$ and its proximal end is of a second diameter $d_y$. Such tapering of the annular cutting member 42 causes the tissue which is cut by the cutting edge 46 to expand as the debulker 14 is advanced, thereby resulting in a more predictable diameter of the resultant channel.

4. Optional Energy-Delivery Features which may be Incorporated into Any of these Tract-Enlarging Systems It will be appreciated that certain types of energy (e.g., laser, radio-frequency energy, electrical resistance heat, etc.) may be delivered to a tract-enlarging apparatus such as the debulker 14, 14a and/or counter-traction member 16, 16a, 16c to enhance the tract-enlarging efficiency of the system. Specific examples of systems which incorporate such energy emitting components are shown in FIGS. 10a–10f.

FIGS. 10a–10c show one energy-emitting debulking-type system which incorporates a bipolar, energy-emitting debulker 14'. FIGS. 10d–10f show another energy-emitting, debulking-type system wherein one electrode is located on an energy emitting debulker 14''' and another electrode is located on an energy-emitting counter-traction member 16'''.

With reference to the particular embodiment shown in FIGS. 10a–10c, the bipolar, radiofrequency debulker 14' comprises an elongate tubular member 40' having a hollow lumen 44' extending longitudinally therethrough. First and second energy-transmitting members 204a, 204b extend longitudinally through the tubular member 44', as shown in the cross sectional view of FIG. 10c. A debulking electrode tip 205 is mounted on the distal end of the tubular member. Such electrode tip 205 incorporates a first radiofrequency-emitting electrode 206 and a second radiofrequency-emitting electrode 208, as shown in FIG. 10b. The first energy transmitting member 204a is connected to the first electrode 206 and the second energy transmitting member 204b is connected to the second electrode 208. An annular insulator body 210 is disposed between the electrodes 204a, 204b. A bipolar radiofrequency generator 200 is connected by way of a wire 202 to the first and second energy transmitting members 204a, 204b such that a circuit is completed between the generator 200 and the respective first and second electrodes 206, 208. Thus, as the debulker is advanced in the distal direction through the interstitial passageway, the generator may be energized to cause radiofrequency current to pass between the annular distal surfaces of the first and second electrodes 206, 208, thereby effecting bipolar cutting or ablation of the tissue which surrounds the interstitial tract.

In the alternative bipolar energy-emitting system shown in FIGS. 10d–10f, the first electrode 206a is mounted on the distal end of the debulker 14" and the second electrode 208a is mounted on the proximal end of the countertraction member 16", as shown. In this embodiment, the first energy transmitting member 204a extends through the tubular member 40" of the debulker 14" while the second energy transmitting member 204b extends through the shaft 60" of the countertraction member 16". Here again, the first energy transmitting member 204a is connected to the first electrode 206a of the second energy transmitting member 204b is connected to the second electrode 208a. In this manner when a bipolar radiofrequency generator 200 is connected to the energy transmitting members 204a, 204b, a circuit is completed between the generator and the first and second electrodes 206a, 208a such that radiofrequency current will pass between the electrodes 206a, 206b in a manner which cuts or ablates the tissue which surrounds the interstitial tract.

As those skilled in the art will appreciate, although bipolar embodiments are shown in FIGS. 10a–10f, similar monopolar embodiments may also be devised through the alternate use of a separate antenna or plate electrode which attaches to the patients body to complete the circuit. Such monopolar embodiments may utilize only a single electrode 204 or 206 to accomplish the desired cutting or ablation of tissue.

Figure 14:
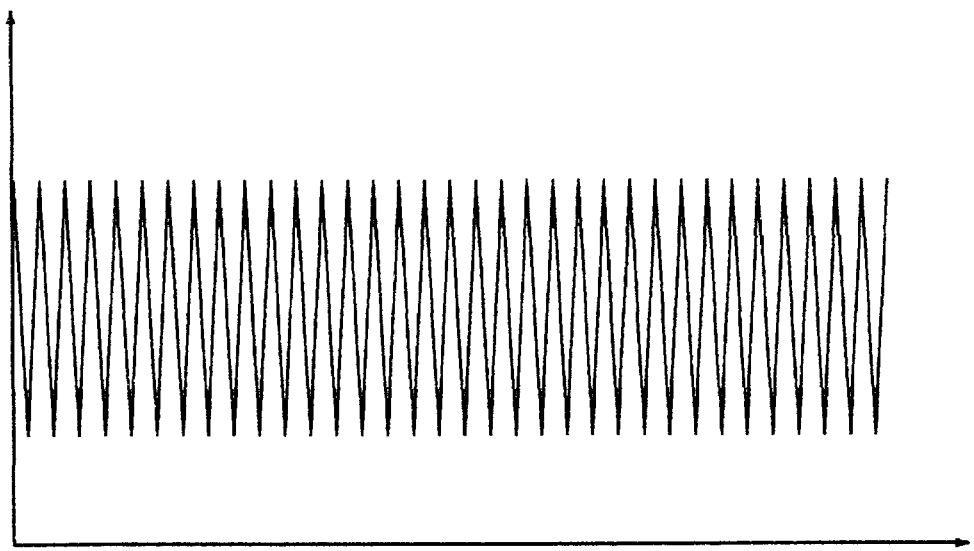
FIG. 14 is a graphic illustration of a continuous emission of radiofrequency energy in accordance with the present invention.

In applications where radiofrequency energy is applied to the debulker 14, 14a, the radiofrequency energy may be applied continuously at 100 KHz–2 MHz, and preferably at about 500 KHx (i.e., 70 watts) until the cutting operation is complete. Alternatively, such radiofrequency energy may be delivered intermittently, in pulsed fashion, to avoid necrosis or damage to the adjacent tissue. Preferably, as illustrated graphically in FIGS. 14a and 14b, when pulsed radiofrequency energy is used in lieu of continuous energy, the duty cycle of the pulsed energy will optomized provide efficient tissue cutting while avoiding damage to surrounding tissue.

Figure 10H:
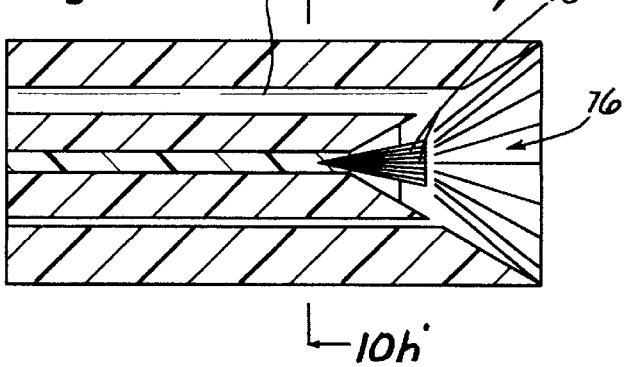
FIG. 10h is a partial side elevational view of another energy-emitting debulker having central laser-transmitting optical fiber (or fiber bundle) in combination with a frusto-conical prism which projects a generally conical pattern of laser light from the distal end of the device.

FIGS. 10g–10i show variants of a laser emitting debulker 14b, wherein laser energy is used to cut or vaporize the tissue. The embodiment shown in FIGS. 10g and 10g' comprises an elongate flexible member having a guidewire lumen 73 extending longitudinally therethrough, and a plurality of longitudinally extending, parallel optical fiber bundles 71 disposed in a generally circular array about the outer perimeter of the member, such optical fiber bundles 71 terminating distally in lenses or other laser emitting surfaces 77 such that a generally conical or annular pattern of laser light is projected from the distal end of the debulker 14b.

FIGS. 10h and 10h' show an alternative laser emitting debulker 14b' wherein a central laser-transmitting optical fiber bundle 75 extends longitudinally a portion of the debulker 14b' and terminates proximal to a generally conical cavity 76 formed in the distal end of the debulker 14b'. A stationary prism 77 having a plurality of light guide grooves 78 formed thereabout, is mounted on the distal end of the fiber bundle 75 such that a generally conical pattern of laser light is projected from the prism, through the conical cavity 76 and out of the distal end of the debulker 14b'. An optional suction lumen 79 may be provided in any of these laser embodiments, to enhance their efficiency (as described more fully herebelow) and/or to aspirate away any residue or tissue particle which become severed during the procedure.

FIGS. 10i and 10i' show another alternative laser emitting debulker 14b'' wherein the central laser-transmitting optical fiber bundle 75' is rotatable, terminates proximal to a generally conical cavity 76 formed in the distal end of the debulker 14b'. A stationary prism 77 having a single light guide groove 78 formed thereon as shown, is mounted on the distal end of the rotatable fiber bundle 75' such that as laser energy is passed through the optical fiber bundle 75' concurrently with its rotation, a generally conical pattern of laser light will be projected from the rotating prism mounted on the end of the rotating fiber bundle 75', and such laser light pattern will be projected through the conical cavity 76' and out of the distal end of the debulker 14b".

4. Optional Application of Negative Pressure Through Debulker Lumen

In either embodiment of the debulking-type system 10, 10a, negative pressure may be applied through the lumen of the debulker 14, 14a to a) tension the tissue being cut so as to improve the cutting efficiency and/or predictability of the cut and/or b) draw the severed tissue into the lumen of the debulker 14, 14a so as to capture and prevent escape of such severed tissue. Additionally, when suction or negative pressure is applied through the lumen of the debulker 14, 14a, the operator may monitor the amount of negative pressure being generated as an indicator of whether the cutting tip 46, 46a is presently in contact with tissue. In this manner, the operator may promptly discern when the cutting tip 46, 46a has passed fully through the desired tissue and into the opposite blood vessel or other cavernous space.

Figure 15:
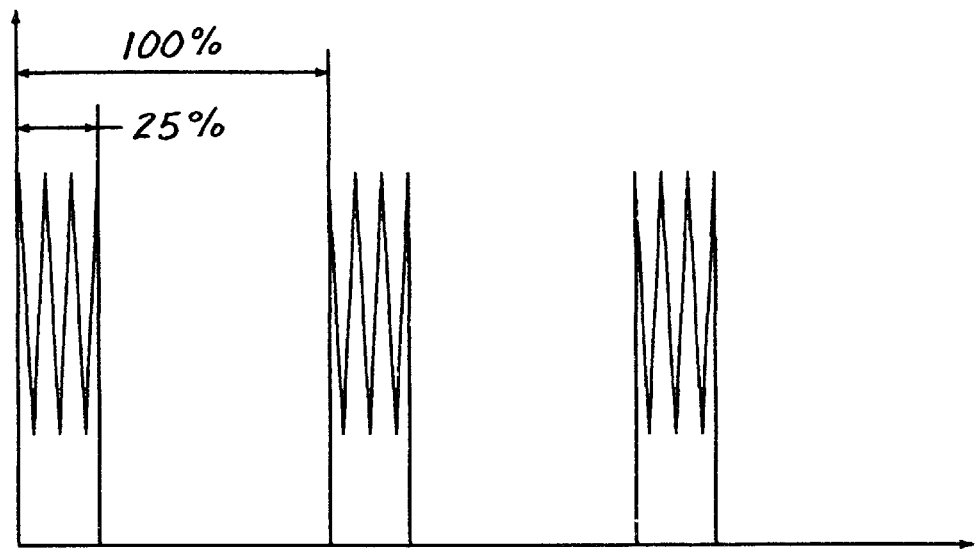
FIG. 15 is a graphic illustration of intermittant or pulsed emission of radiofrequency energy in accordance with the present invention.

5. Optional Apparatus for Enabling Operator to Determine When Debulking Operation is Complete In either debulking-type system 10, 10a, an optional sensor apparatus may be incorporated into the system 10, 10a to provide feedback or signal(s) to enable the operator to determine when the debulking operation is complete so that the advancement or retraction of the debulker 14, 14a may be terminated at an appropriate time. As shown in FIG. 16, the sensor apparatus 126 may comprise any suitable type of sensor which will indicate when the cutting edge 46 of the annular cutting member 42 is no longer in contact With tissue. Examples of the types of sensor apparatus 126 which may be used include sensors which measure impedance, temperature and/or electromagnetic resistance. Additionally, in systems 10, 10a which utilize pulsed energy (FIG. 15) in combination with a temperature sensor 126, the temperature sensed by the sensor 126 may be used to manually or automatically (i.e., by a microprocessor or other controller) adjust the duty cycle of the pulsed energy to avoid exceeding a maximum desired temperature (e.g., the thermal necrosis temperature of the tissue-or some other temperature which has been identified as the maximum temperature to which the surrounding tissue may be heated).

6. Optional Apparatus for Controlling the Force Applied by the Debulker

As shown in FIG. 16, either of the debulking-type systems 10, 10a may include a force controlling apparatus 128 for controlling the force applied by the debulker 14, 14a upon the tissue being severed. In the particular embodiment shown the debulker 14 has a flexible tubular shaft 40 formed of a proximal segment 40a and a distal segment 40b. The distal segment 40b is slidably received within the lumen of the proximal segment 40a, as shown. The force controlling apparatus 128 comprises a spring 130 which is attached to the proximal and distal portions 40a, 40b of the tube 40 such that, when the distal end of the debulker 14 is pressed against tissue, the spring 130 will compress, thereby normalizing or regulating the force which is applied to the tissue. In embodiments where the debulker emits energy (e.g., radiofrequency energy, resistance heat), first and second energy-transmission contacts 132, 134 such that energy will be, emitted from the debulker only when the contacts 132, 134 are in abutment with each other. In this manner, such contact can be maintained only so long as the debulker 14 is engaging tissue, and when the debulker 14 emerges into the other vessel of open space, the spring 130 will relax causing contacts 132,134 to separate and the flow of energy through the debulker 14 to cease.

B. Dilation-Type Systems

FIGS. 12–12c show a dilation-type tract enlarging system 10b of the present invention.

This dilation-type system 10b generally comprises a) a tubular member 120 having a distal tissue-abutting rim 122, and a lumen 124 extending longitudinally therethrough and b) a shaft 126 having a balloon 128 mounted thereon, a guidewire lumen 130 extending longitudinally therethrough, and an inflation/deflation lumen 132 extending from the proximal end thereof to the interior of the balloon. A guidewire which has previously been passed through the penetration tract which is to be enlarged, is inserted into the distal end of the guidewire lumen 130. Thereafter, with the balloon 128 in its deflated state (FIG. 12) and the balloon-bearing portion of the shaft 126 positioned ahead of the tissue abutment rim 122, the system 10b is advanced over the guidewire GW until the tissue abutment rim 122 abuts against or otherwise registers with tissue which surrounds or lies adjacent the proximal end of the penetration tract. Such abutment of the rim 122 against the tissue at the proximal end of the tract will deter further advancement of the system 10b, and will signify to the operator that the balloon 128 has become positioned within the penetration tract. Thereafter, inflation fluid is passed into the balloon 128 through the inflation/deflation lumen 132, causing the balloon 128 to inflate. Such inflation of the balloon serves to dilate the tissue surrounding the penetration tract, thereby accomplishing the desired enlargement of the penetration tract. After the desired dilation of the penetration tract has been completed, the inflation fluid may be withdrawn from the balloon 128 and the system 10b is withdrawn from the body.

C. TISSUE-SLICING TYPE SYSTEMS

FIGS. 17–18b show tissue-cutting tract enlarging catheters 10c of the present invention. These tissue cutting catheters 10c comprise a flexible catheter 700 having a tissue cutting distal tip 702a or 702b mounted thereon.

In the embodiment shown in FIG. 17, the tissue cutting distal tip 702a is a generally cylindrical solid member which has a has a beveled leading edge 704 and a guidewire lumen 706a extending longitudinally therethrough, as shown.

In the embodiment shown in FIGS. 18a–18c, the tissue cutting distal tip 702b has two (2) tapered lateral surfaces 709a, 709b which converge to form a distal end 710. A central guidewire lumen 706b extends through the distal end 710, as shown.

These tissue cutting catheters 10c may be advanced over a guidewire and through a small penetration tract, such that the beveled distal edge 704 or lateral surfaces 706a & 706b will slice or slit the tissue without actually removing any tissue.

D. Two Catheter Tract-Enlarging Systems

Figure 19:
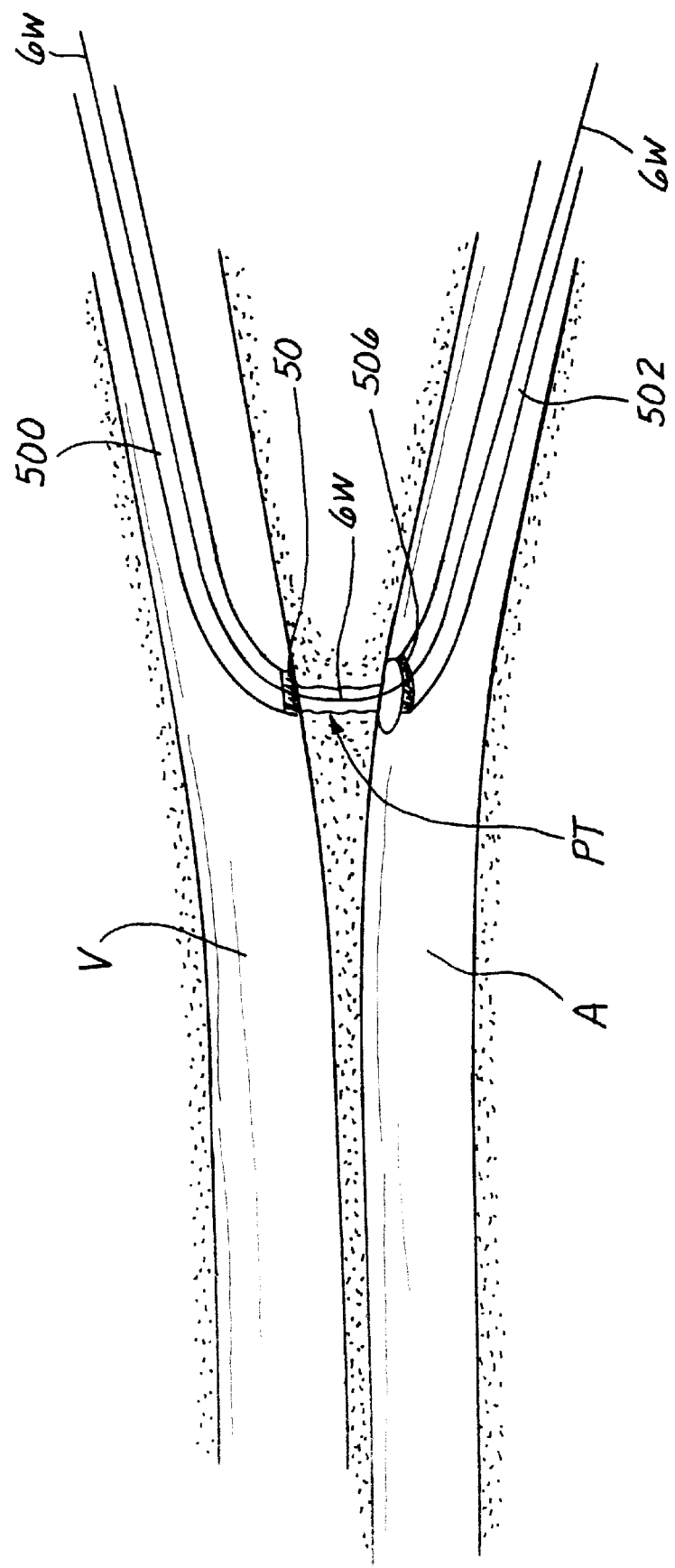
FIG. 19 is a schematic showing of two adjacent blood vessels having a penetration tract formed therebetween, and a two-catheter tract enlarging system of the present invention operatively disposed therein to enlarge the penetration tract.

FIG. 19 shows a two-catheter tract enlarging system 10d which comprises a) a first catheter 500 having a tract-enlarging apparatus (not shown) (e.g., a debulker, dialtor or tissue-slicing member of the above-described nature) advanceable from an opening 504 at or near the distal end of the first catheter 500, and b) a second catheter 502 which has an anvil member 506 (e.g., an abuttable surface or receiving cavity) which is sized and configured to correspond with the leading end of the tract-enlarging apparatus of the first catheter. The first catheter 500 is positioned in one of the anatomical conduits V, and the second catheter is positioned in the other anatomical conduit A, with its anvil member 506 located next to the penetration tract or passageway PT which is to be enlarged. Thereafter, the tract enlarging apparatus (not shown) is advanced through the tract or passageway PT until it registers with (e.g., abuts against or is received with)

the anvil member 506 of the second catheter. As the tract enlarging apparatus (not shown) is being advanced, the anvil member 506 serves to provide counterforce against the tissue adjacent the initially formed tract or passageway PT so as to prevent unwanted protrusion or "tenting" of the tissue into the second anatomical conduit A, and to ensure efficient cutting of the tissue in cases where a debulking or tissue slicing type tract enlarging apparatus is used.

Although exemplary embodiments of the present invention have been shown and described, it will be apparent to those having ordinary skill in the art that c number of changes, modifications, or alterations to the invention as describer herein may be made, none of which depart from the spirit of the present invention. All such changes, modifications and alterations should therefore be seen as within the scope of the present invention as described herein and recited in the following claims.

What is claimed is:

1. A method of enlarging a penetration tract formed between first and second anatomical structures in a human or veterinary patient, the method comprising the steps of:

forming a penetration tract that extends through a wall of the first anatomical structure, through a wall of the second anatomical structure and through any tissue located between the first and second anatomical structures;

passing a guidewire into the penetration tract;

providing an elongate, flexible tubular member having a hollow lumen extending therethrough sized to receive a guidewire, the tubular member having near its distal tip a debulking member including an electrode tip having at least one radio frequency-emitting electrode suitable for ablating tissue;

passing the tubular member over the guidewire and into the penetration tract; and energizing the electrode tip to ablate tissue and enlarge the penetration tract.

2. The method of claim 1, wherein the electrode tip is a monopolar electrode tip having just one electrode, and wherein the method further includes:

providing a second electrode;

contacting the second electrode to an extracorporeal location on the patient to complete an electrode tip circuit.

3. The method of claim 1, wherein the electrode tip is a bipolar electrode tip that includes a pair of the electrodes, and wherein the method further includes energizing the pair of electrodes to generate a radio frequency energy field for ablating tissue.

4. The method of claim 3, wherein the electrode tip includes a distal-most face on which the pair of electrodes are exposed.

5. The method of claim 4, wherein the pair of electrodes are both annular, so that the exposed portions of the electrodes are circular on the distal-most face of the electrode tip.

* * * * *